US010773096B2

(12) United States Patent
Hong et al.

(10) Patent No.: US 10,773,096 B2
(45) Date of Patent: Sep. 15, 2020

(54) METHODS AND SYSTEMS FOR CONTROLLING MAGNETIC FIELDS AND MAGNETIC FIELD INDUCED CURRENT

(71) Applicants: Liyi Elliott Hong, Ellicott City, MD (US); Fow-Sen Choa, Ellicott City, MD (US)

(72) Inventors: Liyi Elliott Hong, Ellicott City, MD (US); Fow-Sen Choa, Ellicott City, MD (US)

(73) Assignees: University of Maryland, Baltimore, Baltimore, MD (US); University of Maryland, Baltimore County, Baltimore, MD (US)

( * ) Notice: Subject to any disclaimer, the term of this patent is extended or adjusted under 35 U.S.C. 154(b) by 179 days.

(21) Appl. No.: 15/740,175

(22) PCT Filed: Jun. 29, 2016

(86) PCT No.: PCT/US2016/040019
§ 371 (c)(1),
(2) Date: Dec. 27, 2017

(87) PCT Pub. No.: WO2017/004156
PCT Pub. Date: Jan. 5, 2017

(65) Prior Publication Data
US 2018/0193658 A1  Jul. 12, 2018

Related U.S. Application Data

(63) Continuation-in-part of application No. PCT/US2015/024054, filed on Apr. 2, 2015.
(Continued)

(51) Int. Cl.
A61N 2/02 (2006.01)
A61N 2/06 (2006.01)
(Continued)

(52) U.S. Cl.
CPC ............... *A61N 2/02* (2013.01); *A61N 2/006* (2013.01); *A61N 2/06* (2013.01); *A61N 2/12* (2013.01)

(58) Field of Classification Search
CPC .................................................. A61N 2/00–12
See application file for complete search history.

(56) References Cited

U.S. PATENT DOCUMENTS 5,691,324 A  11/1997  Sandyk
5,738,625 A   4/1998  Gluck
(Continued)

OTHER PUBLICATIONS

Schlaepfer, T. E., B. Bewernick, S. Kayser and D. Lenz (2011),"Modulating affect, cognition, and behavior—prospects of deep brain stimulation for treatment-resistant psychiatric disorders," Front Integr Neurosci 5: 29.

(Continued)

*Primary Examiner* — Thaddeus B Cox
(74) *Attorney, Agent, or Firm* — Whiteford, Taylor & Preston, LLP; Gregory M. Stone

(57) ABSTRACT

Methods and systems to control magnetic fields and magnetic field induced currents, and to provide stimulations within a patient's body, e.g.: deep brain stimulation, in a non-invasive manner and with greater focus and control than has been afforded by prior known methods and systems. An array of magnetic coils is provided and positionable about a portion of a patient's body, and are configured to create a small region of a magnetic hole, or configured to create a small region of concentrated magnetic field strength, or their combination, and at depths within the patient's body in a focused region and sparing the surrounding tissues of the focused region, that have previously not been receptive to non-invasive TMS methods, which are either focused but can affect only the surface and shadow areas, or that can (Continued)

reach certain depths but by doing so only through affecting large surface areas and deep tissue areas.

15 Claims, 24 Drawing Sheets

Related U.S. Application Data

(60) Provisional application No. 62/186,877, filed on Jun. 30, 2015.

(51) Int. Cl.
*A61N 2/12* (2006.01)
*A61N 2/00* (2006.01)

(56) References Cited

U.S. PATENT DOCUMENTS

| | | |
|---|---|---|
| 5,743,854 A | 4/1998 | Dobson et al. |
| 6,447,440 B1 | 9/2002 | Markoll |
| 7,520,848 B2 | 4/2009 | Schneider et al. |
| 8,267,850 B2 | 9/2012 | Schneider et al. |
| 8,412,332 B2 | 4/2013 | Massoud-Ansari et al. |
| 8,412,344 B2 | 4/2013 | Lee et al. |
| 2004/0066194 A1 | 4/2004 | Slade et al. |
| 2005/0222625 A1 | 10/2005 | Laniado |
| 2007/0027353 A1 | 2/2007 | Ghiron et al. |
| 2009/0254146 A1 | 10/2009 | Bonmassar et al. |
| 2009/0318747 A1 | 12/2009 | Fischell et al. |
| 2010/0185042 A1 | 7/2010 | Schneider et al. |
| 2010/0256438 A1 | 9/2010 | Mishelevich et al. |
| 2010/0286468 A1 | 11/2010 | Mishelevich et al. |
| 2010/0331602 A1 | 12/2010 | Mishelevich et al. |
| 2011/0184223 A1 | 7/2011 | Peterchev et al. |
| 2012/0053449 A1 | 3/2012 | Moses et al. |
| 2013/0096363 A1 | 4/2013 | Schneider et al. |
| 2013/0317279 A1 | 11/2013 | Khizroev et al. |
| 2014/0081072 A1 | 3/2014 | Huang et al. |
| 2014/0249352 A1 | 9/2014 | Zangen et al. |
| 2014/0276182 A1 | 9/2014 | Helekar et al. |
| 2015/0025297 A1* | 1/2015 | Pan ........................ A61N 2/006 600/13 |
| 2016/0193476 A1* | 7/2016 | Helekar ................. A61N 2/006 600/544 |

OTHER PUBLICATIONS

Hoffman, R. E., R. Gueorguieva, K. A. Hawkins, M. Varanko, N. N. Boutros, Y. T. Wu, K. Carroll and J. H. Krystal (2005), "Temporoparietal transcranial magnetic stimulation for auditory hallucinations: safety, efficacy and moderators in a fifty patient sample," Biol Psychiatry 58(2): 97-104.

Jin, Y., S. G. Potkin, A. S. Kemp, S. T. Huerta, G. Alva, T. M. Thai, D. Carreon and W. E. Bunney, Jr. (2006), "Therapeutic effects of individualized alpha frequency transcranial magnetic stimulation (alphaTMS) on the negative symptoms of schizophrenia," Schizophr Bull 32(3): 556-561.

Roth, Y., A. Amir, Y. Levkovitz and A. Zangen (2007), "Three-dimensional distribution of the electric field induced in the brain by transcranial magnetic stimulation using figure-8 and deep H-coils," J Clin Neurophysiol 24(1): 31-38.

Deng, Z. D., S. H. Lisanby and A. V. Peterchev (2013), "Coil design considerations for deep transcranial magnetic stimulation," Clin Neurophysiol.

Roth, Y., G. S. Pell and A. Zangen (2013), "Commentary on: Deng et al., Electric field depth-focality tradeoff in transcranial magnetic stimulation: simulation comparison of 50 coil designs," Brain Stimul 6(1): 14-15).

International Search Report issued in corresponding PCT Application No. PCT/US15/24054 dated Jul. 10, 2015.

International Search Report issued in corresponding International Patent Application No. PCT/US2016/40019 dated Sep. 26, 2016.

Supplementary European Search Report issued in co-pending European Application No. 15773730.5 dated Sep. 14, 2017.

Du, Xiaoming, et al. Neural Summation in Human Motor Cortex by Subthreshold Transcranial Magnetic Stimulations. Experimental Brain Research, DOI 10.1007/s00221-014-4146-z, Nov. 2014.

* cited by examiner

Prior-art (a)

Prior-art (b)

Prior-art (c)

Fig. 4
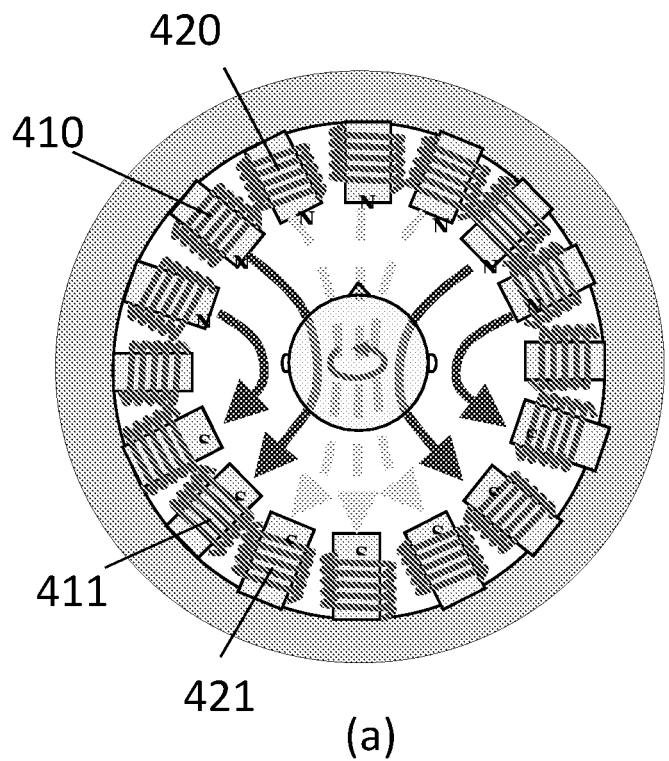
(a)
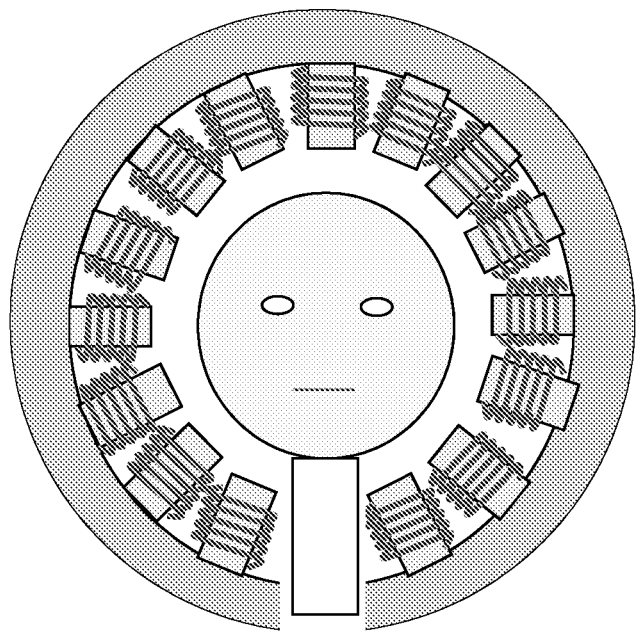
(b)

(a) (b) (c)

(a) (b) (c) (d)

Fig. 13
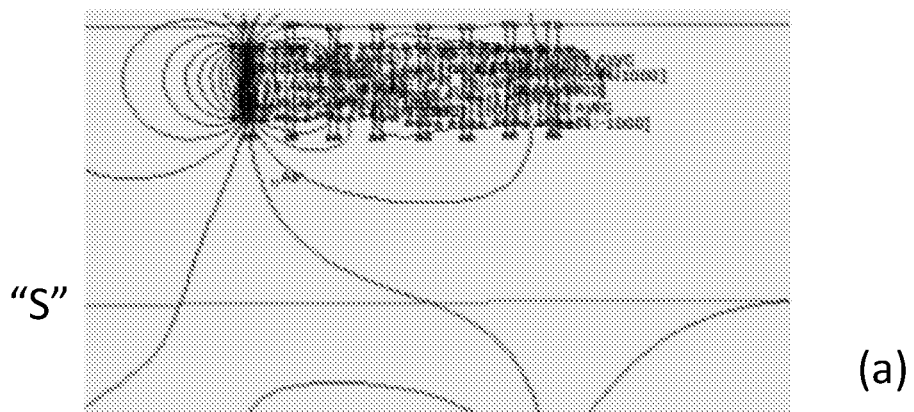
"S"
(a)
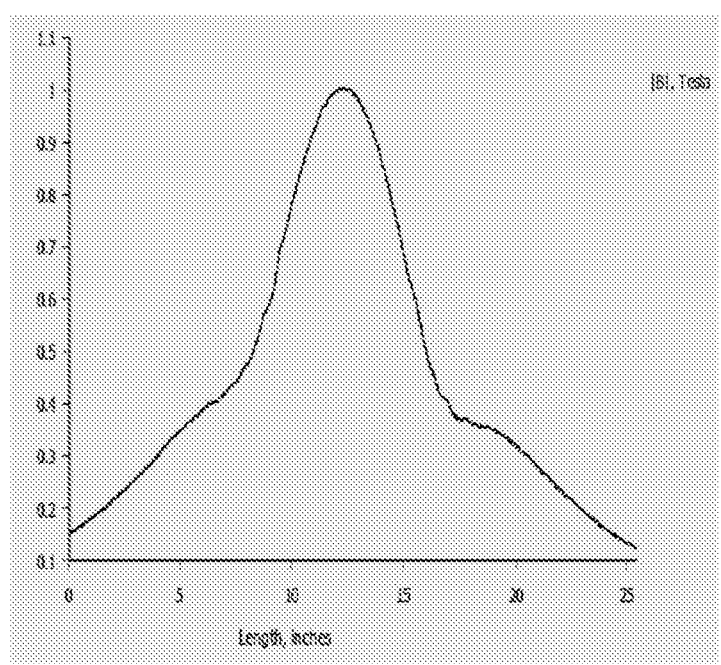
(b)

Fig. 14
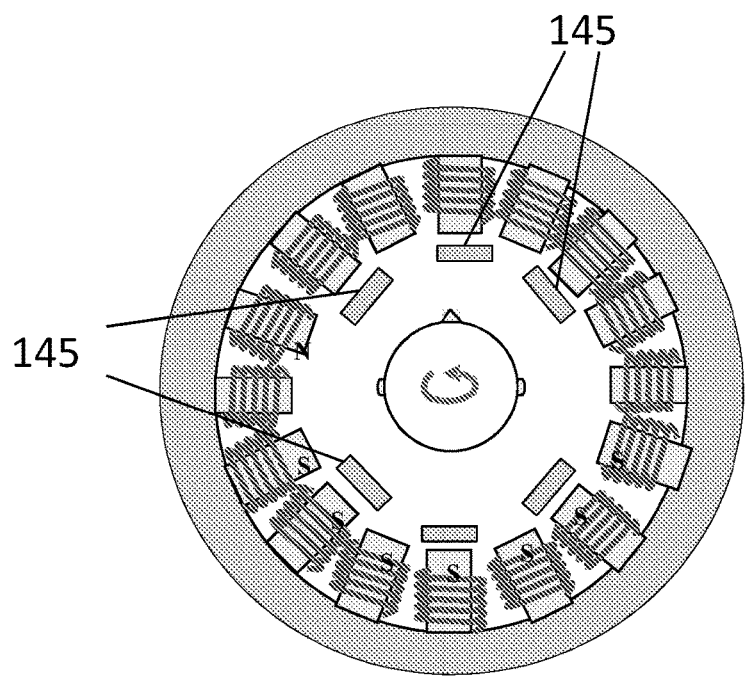
(a)
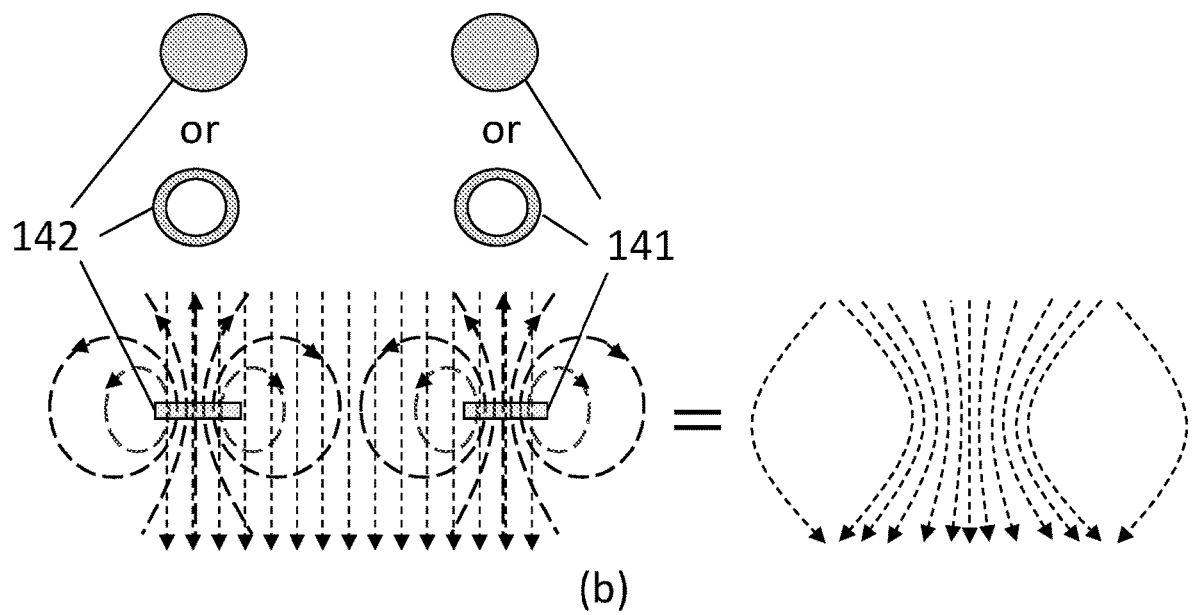
(b)

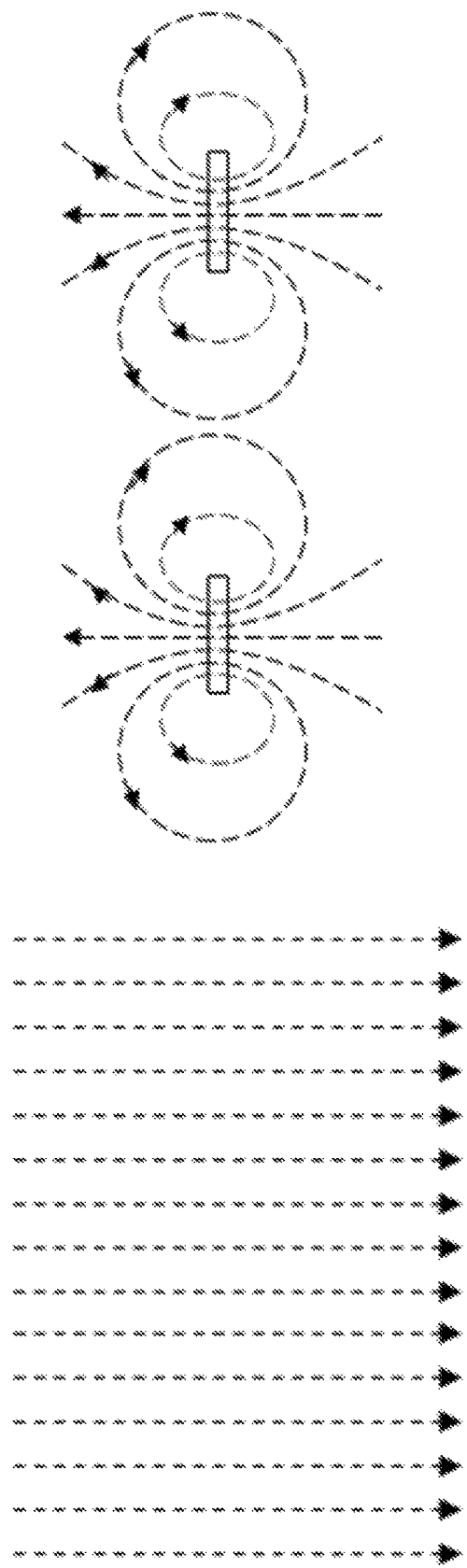
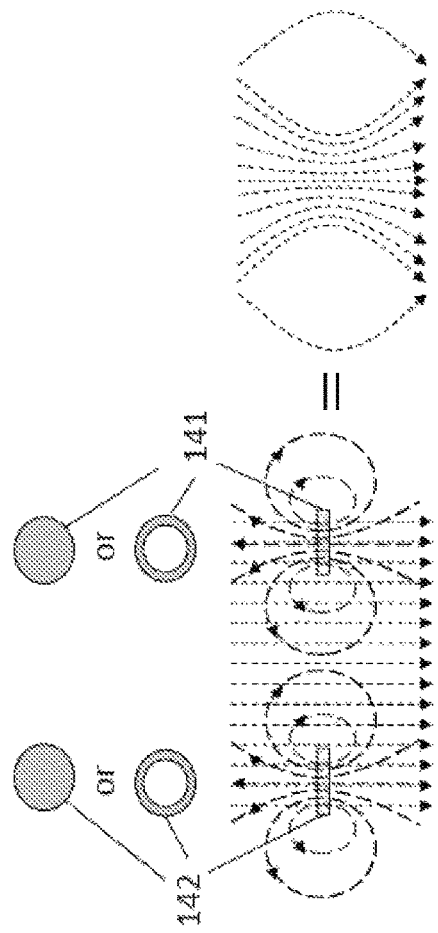
Fig. 20 (a)
Fig. 20 (b)
Fig. 20 (c)

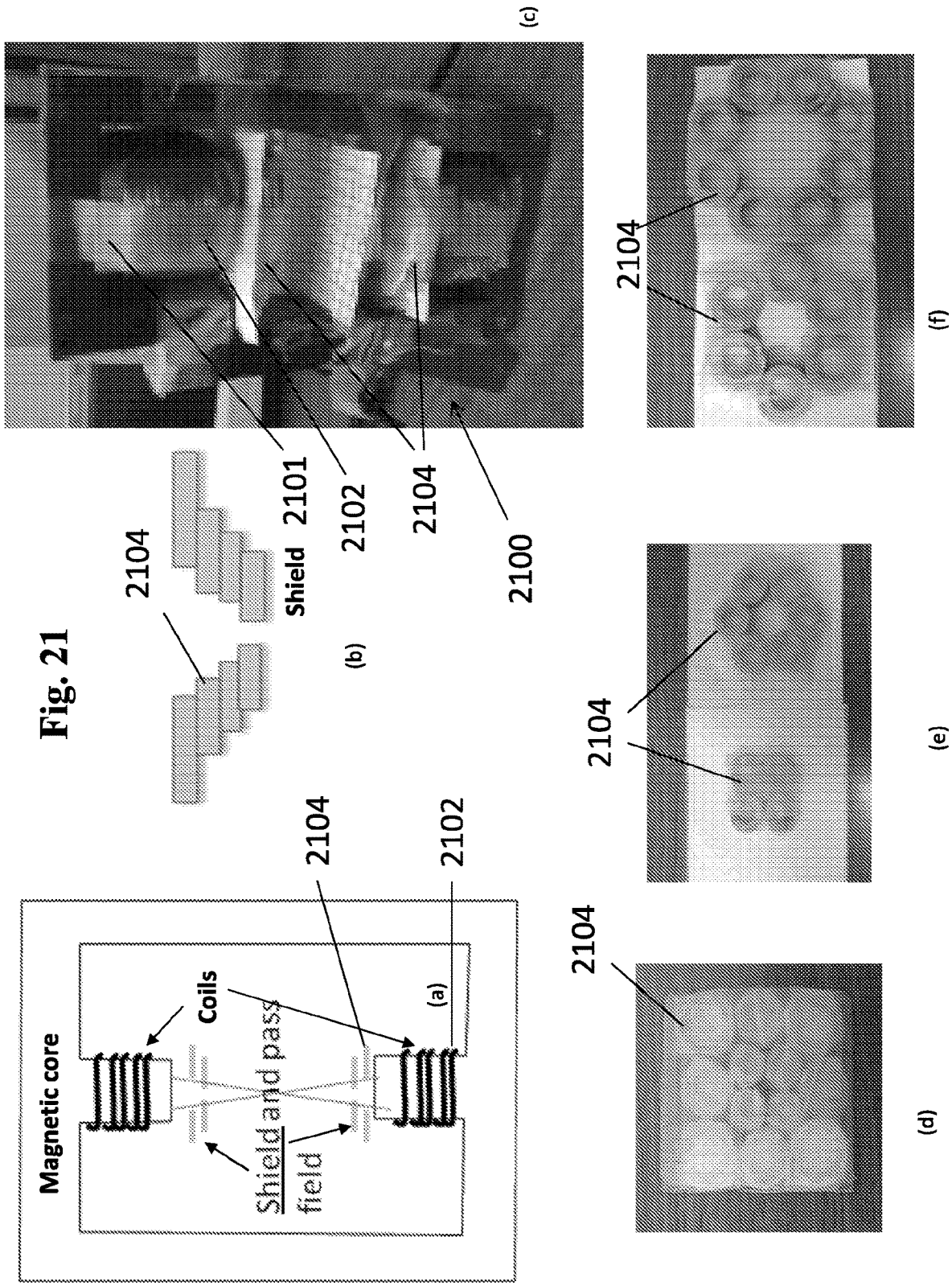

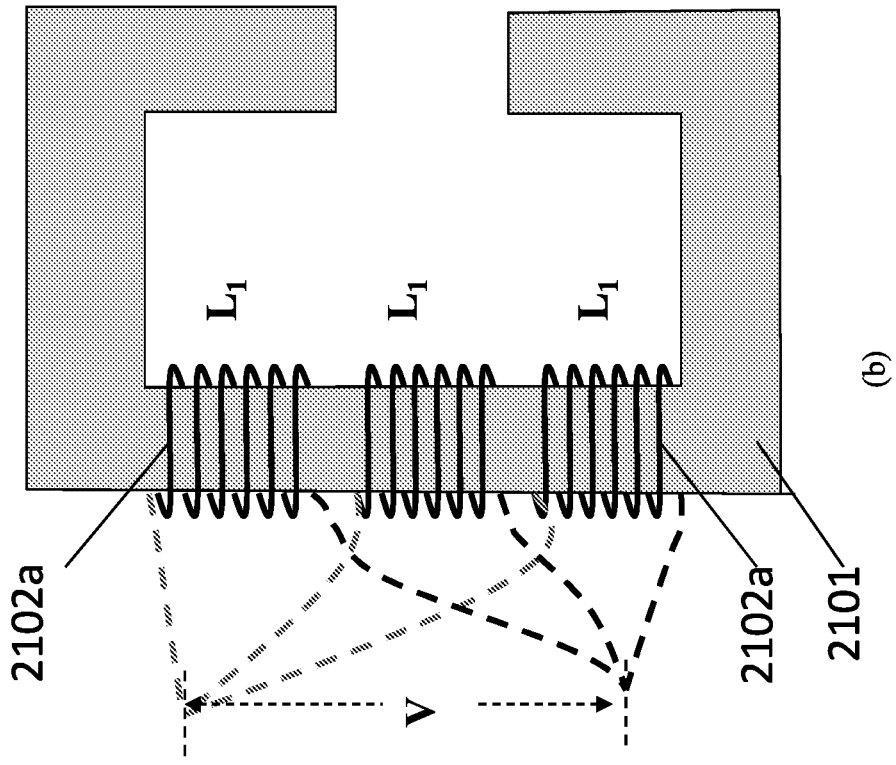
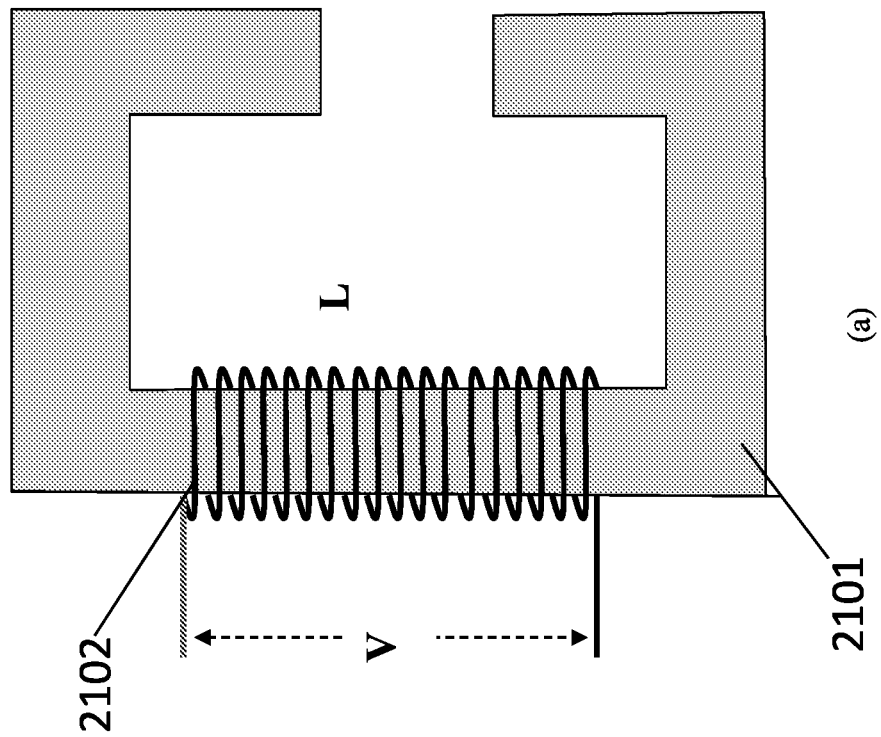
Fig. 24

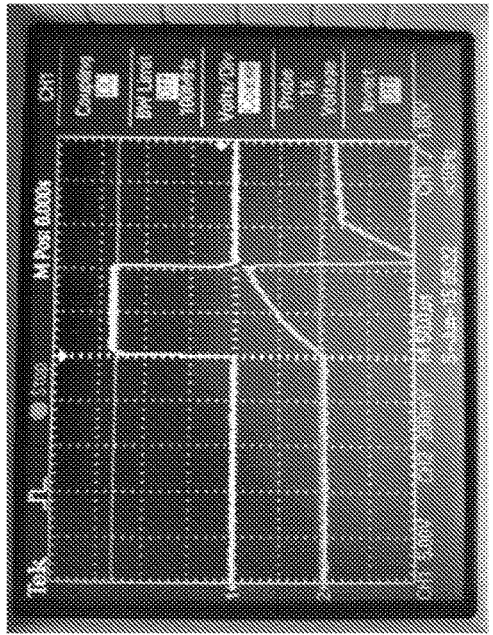
(b) Single coil 100 turns (200mV scale)
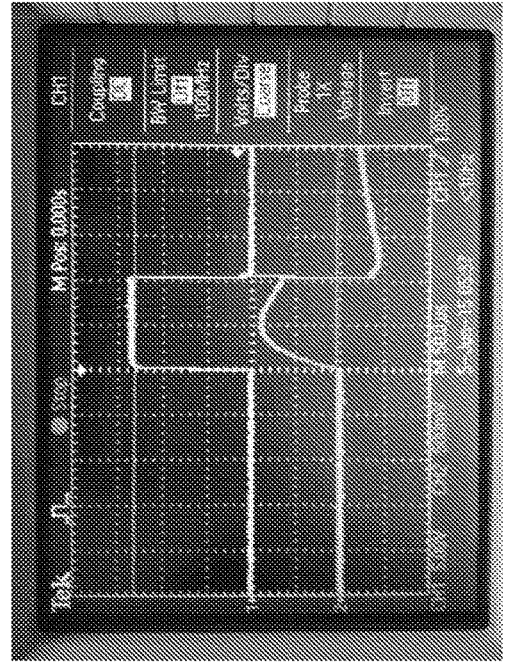
(d) 10*10 turns coil (500mV scale)
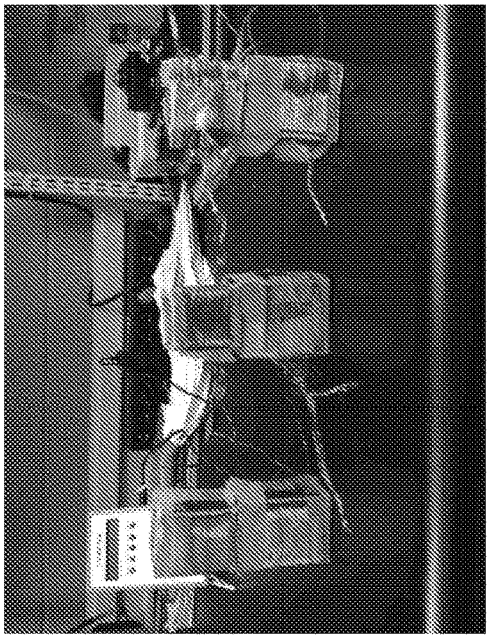
(a) 3 types coil pairs (b-d) for stimulator at Fig 21(c)
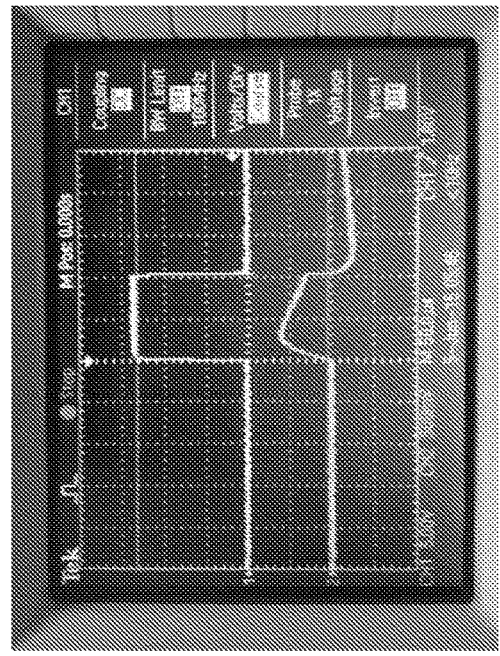
(c) 20*5 turns coil (500mV scale)
Fig 25

METHODS AND SYSTEMS FOR CONTROLLING MAGNETIC FIELDS AND MAGNETIC FIELD INDUCED CURRENT

CROSS REFERENCE TO RELATED APPLICATIONS

This application is based upon and claims priority from United States Provisional Patent Application No. 62/186,877, titled "Methods and Systems for Controlling Magnetic Fields and Magnetic Field Induced Current" and filed on Jun. 30, 2015 by the inventors herein, which is hereby incorporated by reference for all purposes as if fully set forth herein. This application is also based upon and claims priority from International Patent Application No. PCT/US15/24054, titled "Methods and Systems for Controlling Magnetic Fields and Magnetic Field Induced Current" and filed on Apr. 2, 2015, which International Patent Application claims priority from U.S. Provisional Patent Application No. 61/973,944, filed on Apr. 2, 2014 by the inventors herein, which applications are hereby likewise incorporated by reference for all purposes as if fully set forth herein.

FIELD OF THE INVENTION

The present invention relates generally to the control of magnetic fields, and more particularly to methods and systems for controlling a transient magnetic field using one or more DC magnetic fields to provide magnetic stimulation to a patient's body.

BACKGROUND

In recent years, deep brain stimulation (DBS) has shown a great potential as an effective treatment for many neurological and neurodegenerative diseases. DBS is already FDA-approved as a treatment for a variety of diseases, such as essential tremor, Parkinson's disease, and dystonia. DBS has also been tested or proposed as a remedy for a variety of disorders, such as chronic pain, major depression, obsessive-compulsive disorder, dementia and schizophrenia (See, e.g., Schlaepfer, T. E., B. Bewernick, S. Kayser and D. Lenz (2011), "Modulating affect, cognition, and behavior—prospects of deep brain stimulation for treatment-resistant psychiatric disorders," Front Integr Neurosci 5: 29; Hoffman, R. E., R. Gueorguieva, K. A. Hawkins, M. Varanko, N. N. Boutros, Y. T. Wu, K. Carroll and J. H. Krystal (2005), "Temporoparietal transcranial magnetic stimulation for auditory hallucinations: safety, efficacy and moderators in a fifty patient sample," Biol Psychiatry 58(2): 97-104; Jin, Y., S. G. Potkin, A. S. Kemp, S. T. Huerta, G. Alva, T. M. Thai, D. Carreon and W. E. Bunney, Jr. (2006), "Therapeutic effects of individualized alpha frequency transcranial magnetic stimulation (alphaTMS) on the negative symptoms of schizophrenia," Schizophr Bull 32(3): 556-561; and Kuhn, J., M. Bodatsch, V. Sturm, D. Lenartz, J. Klosterkotter, P. J. Uhlhaas, C. Winter and T. O. Grundler (2011), "[Deep brain stimulation in schizophrenia]," Fortschr Neurol Psychiatr 79(11): 632-641). In many cases, DBS treatment seems to be able to stop or slow the disease process and improve symptoms and functioning for patients. Although DBS appears to be quite promising, it is still an invasive method and requires brain surgery through the skull and insertion of electrodes into deep brain regions. Such surgery can potentially damage existing functional brain cells and is usually performed as a last resort. The situation has not only restricted the number of patients treated, but has also limited the opportunity to explore the full potential of the technique. Transcranial magnetic stimulation (TMS) is a non-invasive brain stimulation method.

TMS uses transient pulse field induced currents to cause neuronal depolarization and hyperpolarization in brain cortices. It induces a small electrical current, which stimulates nerve cells including their branches and allows for the study of brain functions and the development of new treatments for brain disorders. Currently available coil designs struggle with the inability to stimulate the brain in a focused region and at the tissue depths necessary to treat the foregoing diseases and disorders. Commonly used coils, including the circular coil shown in FIG. 1(a), and the so-called FIG. 8 coils shown in FIG. 1(b), can only stimulate superficial areas of the brain (Roth, Y., A. Amir, Y. Levkovitz and A. Zangen (2007), "Three-dimensional distribution of the electric field induced in the brain by transcranial magnetic stimulation using figure-8 and deep H-coils," J Clin Neurophysiol 24(1): 31-38; Deng, Z. D., S. H. Lisanby and A. V. Peterchev (2013), "Coil design considerations for deep transcranial magnetic stimulation," Clin Neurophysiol; and Roth, Y., G. S. Pell and A. Zangen (2013), "Commentary on: Deng et al., Electric field depth-focality tradeoff in transcranial magnetic stimulation: simulation comparison of 50 coil designs," Brain Stimul 6(1): 14-15). The only approved and commercially available coil known to the inventors that is promoted as a deep brain TMS is the H-coil TMS, as shown by FIG. 1(c), by Brainsway of Jerusalem, Israel. However, the H-coil and its variants still generate currents that mostly circulate around the outer region of the brain, causing some increased depth of stimulation through summation, but also undesirably affecting much wider cortical regions of the brain (Roth et al. 2007). Loss of focality is a trade-off for depth in H-coils as in all other coils currently available or conceived and known to the inventors (Denget al. 2013; Roth et al. 2013; Roth et al. 2007). Another limitation of some of these previous coils is that they require factory-wired configurations and can only target one predetermined area per coil. The hardware-to-brain inflexibility limits research and clinical applications, which often require testing of different anatomic locations, or personalized localization in different patients to achieve maximum benefit. Thus far, of the previously known devices that are known to the inventors, the figure-8 coil has the best combination of focality and depth. Its focality is achieved by summing one clockwise and one counter-clockwise circular field at the middle, making the focality of the induced currents more predictable. However, the resolution is modest and the stimulation does not go very deep. Therefore, current non-invasive TMS methods are receptive to other modestly focused stimulation, but only at the surface and shadow areas (e.g., FIG. 8 coils or their variants), or reaching certain depths but doing so only through affecting large surface areas and deep tissue areas (e.g., H-coils or their variants). This is because these methods currently available or conceived and known to the inventors do not have the technical means to practically escape the trade-off between focality and depth (Denget al. 2013; Roth et al. 2013; Roth et al. 2007).

In light of the foregoing limitations, there is a need for methods and systems that provide noninvasive controllable DBS, and also stimulations that are capable of operating effectively deep within a focal region or regions of the body while leaving the tissues outside of the desired focal area unaffected. However, achieving the above purposes and/or benefits is not a necessary feature to each of the exemplary embodiments, and claims may recite subject matter that does not achieve the above stated purpose.

SUMMARY OF THE INVENTION

Disclosed herein are methods and systems to control magnetic fields and magnetic field induced currents, and more particularly to provide stimulations within a patient's body, such as deep brain stimulation, in a non-invasive manner and with greater focus and control than has been afforded by prior known methods and systems. In accordance with certain aspects of an embodiment, an array of magnetic coils is provided and positionable about a portion of a patient's body.

During operation of an embodiment of the invention, at least some of the magnetic coils function as DC coil pairs configured to generate a DC magnetic field, while at least some of the other magnetic coils function as transient magnetic field generators to generate an induced current within a portion of the patient's body, such as in a region of the patient's brain. Such system is configured so that the DC magnetic fields may be used to manipulate the transient magnetic field induced current, in turn allowing significantly improved control and focus of the induced current within a specifically desired volume of interest within a patient's body.

With respect to certain aspects of an embodiment of the invention, the magnetic coils are provided on a housing and positioned with respect to a second magnetic source that may be configured to create a small region of a magnetic hole (i.e., a small area or volume within a target region in a patient's body in which an induced magnetic field applied to that target region creates an impact sufficient to cause a neuronal response, while areas or volumes surrounding such small area or volume receive negligible impact), or configured to create a small region of concentrated transient magnetic field strength, and particularly at depths within the patient's body that are desired to be receptive to TMS stimulation.

In accordance with certain aspects of an embodiment of the invention, a system for controlling magnetic fields in a target volume inside of a patient's body is provided, comprising: a first magnetic field source comprising at least a first pair of magnetic coils disposed on an external housing and positioned a distance apart from one another to define an open space between the first pair of magnetic coils, wherein the open space is sized to receive a portion of a patient's body, the first pair of magnetic coils being configured to generate a first magnetic field extending through the open space so as to intercept the portion of a patient's body; a second magnetic field source configured to superpose with the first magnetic field and conform a shape of a resulting combined first magnetic field to a predetermined desired shape at a target location at which the combined magnetic field interacts with the portion of a patient's body and at any depth into that portion of a patient's body that is positioned in the open space; a power source in electrical communication with the first magnetic field source; and a control system in electrical communication with the power source.

BRIEF DESCRIPTION OF THE DRAWINGS

The above and other aspects, features and advantages of the disclosed exemplary embodiments will be more apparent from the following detailed description taken in conjunction with the accompanying drawings in which:

FIGS. 4 (a) and (b) show schematically a horizontal and a vertical cross-section through a magnetic stimulator system according to an exemplary embodiment of the invention.

FIGS. 13 (a) and (b) show a schematic view of simulation results for a configuration of a magnetic field in a coil system according to another exemplary embodiment of the invention.

FIGS. 14(a) and (b) show a magnetic stimulation system including magnetic shields and the effects of magnetic shields on an externally applied magnetic field according to another exemplary embodiment of the invention.

FIG. 17(c) shows a uniform B-field distribution (marked B1) being added together with a reverse direction field produced from a smaller diameter coil pair (marked B2), and added to an array of coil pairs surrounding the small diameter coil pair (marked B3). FIG. 17(d) shows superposing all 3 fields together to obtain the composite field as shown in FIG. 17(d). FIG. 17(e) is a top-down view of all 3 spatial domain Fourier components and their field contribution. FIG. 17(f) shows simulation results for a configuration of a magnetic field resulting from the system shown in FIGS. 17(d) and 17(e) according to an exemplary embodiment of the invention. By adjusting amplitudes of the 3 different spatial Fourier components, a "hole" shape magnetic field distribution may be obtained. FIG. 17(f) is color coded such that the red color represents a strong magnetic field and blue represents a weak magnetic field.

FIG. 20(a) shows a schematic view of an initial transient magnetic field.

FIG. 20(b) shows a schematic view of an induced current generated transient magnetic field from an array of conductive rings or disks.

FIG. 20(c) shows a schematic view of a summation of the initial transient magnetic field of FIG. 20(a) and the induced transient magnetic field of FIG. 20(b) to produce a combined field that is more focused in the center "hole" region.

FIG. 21(a) is a schematic view of a stimulator structure having one pair of coils and shield in accordance with certain aspects of an embodiment of the invention.

FIG. 21(b) is a schematic view of an exemplary metal shield for use with the stimulator structure of FIG. 21(a) and composed of 4 layers of metal rings or disks.

FIG. 21(c) is a photograph of an exemplary one-coil-pair stimulator in accordance with FIGS. 21(a) and (b).

FIGS. 21(d)-(f) are exemplary configurations of metal ring or disk shields according to certain aspects of an embodiment of the invention. The number of pairs, layers and types of the metal rings or disk shields may vary.

FIG. 22 shows measured electric field strength distribution along the x-y planes (perpendicular to the up-down, z-direction). More particularly.

FIG. 24(a) is a schematic view of a single coil serial connection.

FIG. 24(b) is a schematic view of a parallel connection of sub-divided smaller coils to obtain reduced driving voltage in accordance with certain aspects of an embodiment of the invention.

FIG. 25(a) is a photograph of three different wire wrapping configurations and connection to a stimulator configured in accordance with FIG. 21(c). FIG. 25(b) shows the results of using a 100 turn single coil. FIG. 25(c) shows the results of using 5 parallel coils each with 20 turns of wire. FIG. 25(d) shows the results of using a 10 parallel coils each with 10 turns of wire. In each of FIGS. 25(b)-(d), the yellow trace represents the driving voltage signal into the coils. The blue traces represent the generated magnetic/electric field signals under different coil structures and connections.

DETAILED DESCRIPTION

The following detailed description is provided to gain a comprehensive understanding of the methods, apparatuses and/or systems described herein. Various changes, modifications, and equivalents of the systems, apparatuses and/or methods described herein will suggest themselves to those of ordinary skill in the art. Descriptions of well-known functions and structures are omitted to enhance clarity and conciseness.

The invention is described with reference to the drawings in which like references are labeled with like numerals. The relationship and functioning between the various elements are better understood by reference to the figures. However, the embodiments described herein are examples only and the invention is not limited to those specifically described or depicted in the figures. It should also be understood that the figures are not drawn to scale and in some instances details that are not necessary for the understanding of the present invention are omitted such as common methods of manufacturing. Furthermore, it should be understood that the invention described herein is generally described in terms of a deep brain stimulation system and method. However, it should be understood that that the systems and methods of the present invention may be used for a wide range of uses including to stimulate other areas of the brain and body. One having ordinary skill in the art would recognize minor changes that would be necessary to adapt the system for different uses. These modifications should be considered part of the invention because they do not deviate from its overall spirit. The drawings are two-dimensional, although the invention is for both two-dimensional and three-dimensional designs for coil arrangement. The description and drawings are based on one or a few coils in one configuration, although the invention may provide dozens, hundreds, or thousands of coils in combination within one configuration.

(A). A Configuration of the System for Controlling Magnetic Fields

Figure 2:
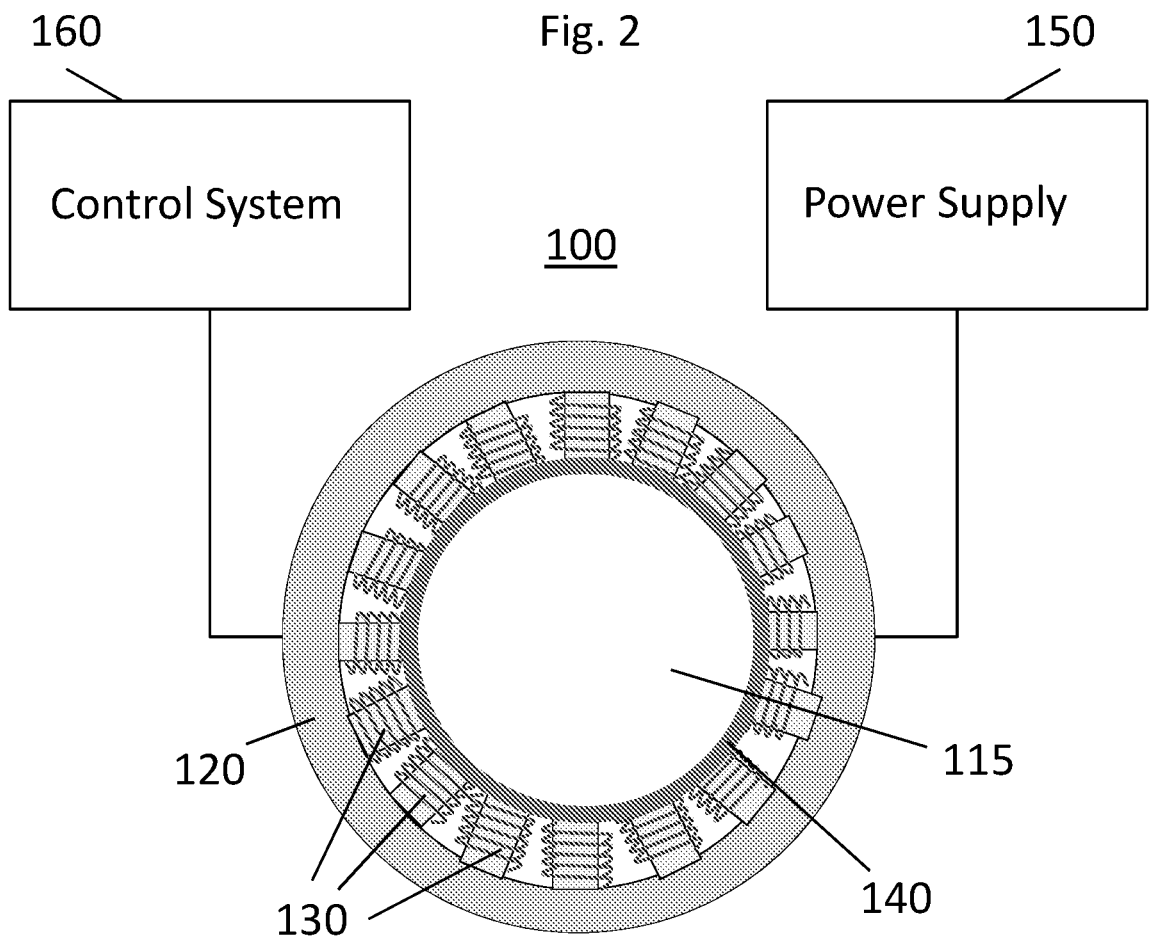
FIG. 2 shows a schematic view of a magnetic stimulator system according to an exemplary embodiment of the invention.

Referring now to the figures, FIG. 2 illustrates one potential configuration of a magnetic stimulator system 100. System 100 comprises a plurality of magnetic coils 130 configured to generate magnetic fields in a region of interest, the coils 130 being arranged in arrays; power supply 150; and a control system 160 configured to control the currents in the coils, thereby controlling the magnetic fields generated by the coils. The coil-array comprises an external housing 120 that has a central cavity 115, which is sized to fit a living organism's head, torso, limb, or other body part. The housing may be domed shaped, as shown in FIG. 4(b), if it is specifically configured for a head, or it may be generally cylindrical with openings on either end. More generally, the physical structure of the array can be in the shape of a helmet, a dome, a donut, or other shapes conforming to specific body parts. The physical structure may also comprise several separate arrays each containing multiple coils, and the arrays may be arranged in various spatial locations. FIGS. 4(a) and (b) show schematically a horizontal and a vertical cross-section through a magnetic stimulator system 100 according to certain aspects of an exemplary embodiment. Four or more magnetic coils (poles) 130 are located on the inner wall of the housing. At least two poles are used to generate a DC magnetic field (e.g., DC coils 410 and 411 in FIG. 4(a)) and at least two poles are used to generate the transient magnetic field (e.g., coils 420 and 421 in FIG. 4(a)). During the course of a procedure, a pole may be used as both a DC field generator and a transient magnetic field generator at different times. The coils may be driven in pairs (as shown in FIG. 4(a)) such that one coil corresponds to a north pole and the other to a south pole (e.g., coils 420 and 421).

A useful construct for expressing the behavior of the magnetic fields induced by the coils is the "beam" or "beams" associated with the magnetic field. Generally, a beam is defined by a path of higher power or higher amplitude regions of a vector field distribution. For example, while a laser output intensity distribution spreads from minus infinity to positive infinity, the skilled artisans refer to the fact that the laser has a finite beam spot size. There are multiple ways of defining the "beam spot size" of a laser field (and other vector fields). An often used way of defining the beam is by the "full wave half maximum (FWHM)," where the half power points are taken as the diameter of the beam. Anything inside the radius is called "laser beam covered area," while regions outside of the radius are often neglected. Other ways of defining the beam include taking the points having power equal to 1/10 of the peak power as the beam diameter, or by taking the points having power of 1/e of the peak power. The invention set forth herein is not limited by the particular way a beam can be defined.

Figure 3:
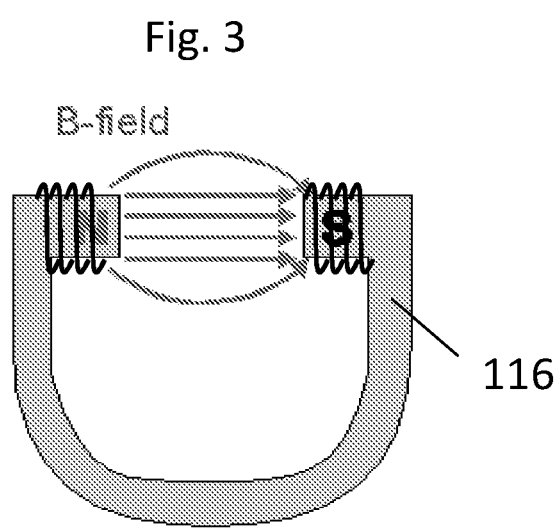
FIG. 3 shows a schematic view of a two coil system disposed on a magnetic core according to an exemplary embodiment of the invention.

In accordance with certain aspects of an exemplary embodiment, the magnetic coil poles may be disposed on a magnetic core as shown in FIG. 3. The magnetic core may comprise an iron core (having magnetic permeability about 200,000 times larger than air) or other magnetic materials known to have high magnetic permeability. The magnetic system may be designed so as to ensure that the magnetic field flux generated by the coils is kept as much as possible inside of the high permeability core material. Keeping the magnetic flux in the high permeability region makes possible the generation of high magnetic fields by relatively small electrical currents into the coils. However, all magnetic stimulators will need to have a region passing through nonmagnetic materials. Minimizing this region will minimize the driving electrical current. Thus, using more iron core along the magnetic path reduces magnetic resistance. In turn, smaller magnetic resistance enables the use of low driving currents to achieve high magnetic fields. This will help to reduce power consumption and minimize heating problems.

The housing 120 may be made of iron core material, or other high permeability materials, such as to reduce magnetic resistance. To obtain higher magnetic fields, superconducting materials that can achieve high dynamic ranges of control may be used to reduce the risk of heating and mechanical stress. If iron core is used, a nonmetallic inner liner 140 may be welded inside to provide additional strength. The inner liner and external housing may contain ventilation, temperature control, noise and/or heat reduction apparatus, and access holes for monitoring a human participant, recording additional information, and increasing safety and patient comfort.

The magnetic coil poles may be positioned on the magnetic system 100 to create a two or three dimensional field. When generating a three dimensional field, the magnetic coil array may be stationary and variation of the field will be controlled by the poles. The precise positioning between the array and the human subject can be obtained by moving the subject using a controlled stretcher, chair, or a similar device, or by moving the array with respect to the subject. If a two dimensional field is used, the magnetic coil array may be moved along the z axis, allowing for targeting within a volume. Securing mechanisms (not depicted), such as straps or braces, will be located within or around the magnetic coil array to keep the target area in place during treatment.

(B). Stimulating Brain Cells by Electric Currents Induced by Short Pulses of Transient Magnetic Fields (Achieving Neural Firing Threshold).

Transcranial magnetic stimulation (TMS) is a non-invasive brain stimulation method. TMS uses transient field induced currents to cause neuronal depolarization and hyperpolarization in brain cortices. It induces a small electrical current, which stimulates nerve cells including their branches and allows for the study of brain functions and the development of new treatments for brain disorders.

When a perturbation of the neuronal cell membrane takes place, the voltage across the membrane will change. When the change is making the potential inside the cell less negative, this is called a depolarization process. In a depolarization process, when the potential difference is close to −55 mV (exact number varies from cell to cell), a depolarization chain reaction process occurs where the potential inside a cell will become less negative, then fully depolarized to even positive, and then go back to negative values becoming polarized again. This process is called neuron firing or action potential generation. In a conductive material, such as tissue or a nerve cell body, an electrical field will create a current $J=\sigma E$, and part of the current will charge the membrane capacitor to change the ~−70 mV polarization voltage to a more positive value. When the polarization voltage is close to ~−55 mV, the action potential chain reaction starts to take place. This −55 mV polarization voltage is called action potential threshold or neuronal firing threshold.

Among others, the purpose of the systems and methods described herein is to generate currents capable of causing neuronal depolarization and hyperpolarization (or causing neuronal firing and pulse action potential) only into a certain (preferably small) target volume of the brain.

(C). Methods of Operating the Magnetic System to Obtain Neuronal Firing Only or Primarily in a Target Volume (Confine the Induced Currents into the Target Area).

Figure 1:
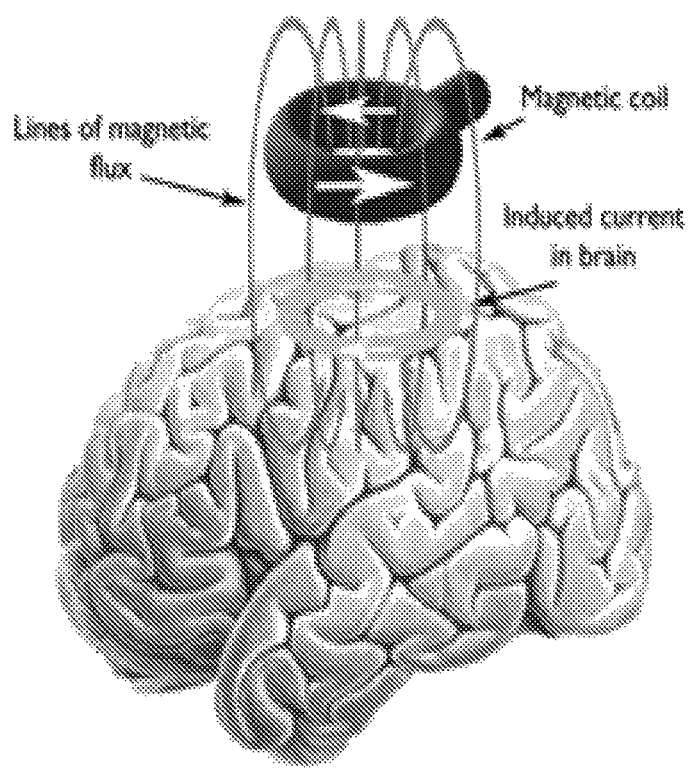
FIGS. 1(a) to (c) show a schematic view of prior art devices.
Figure 1:
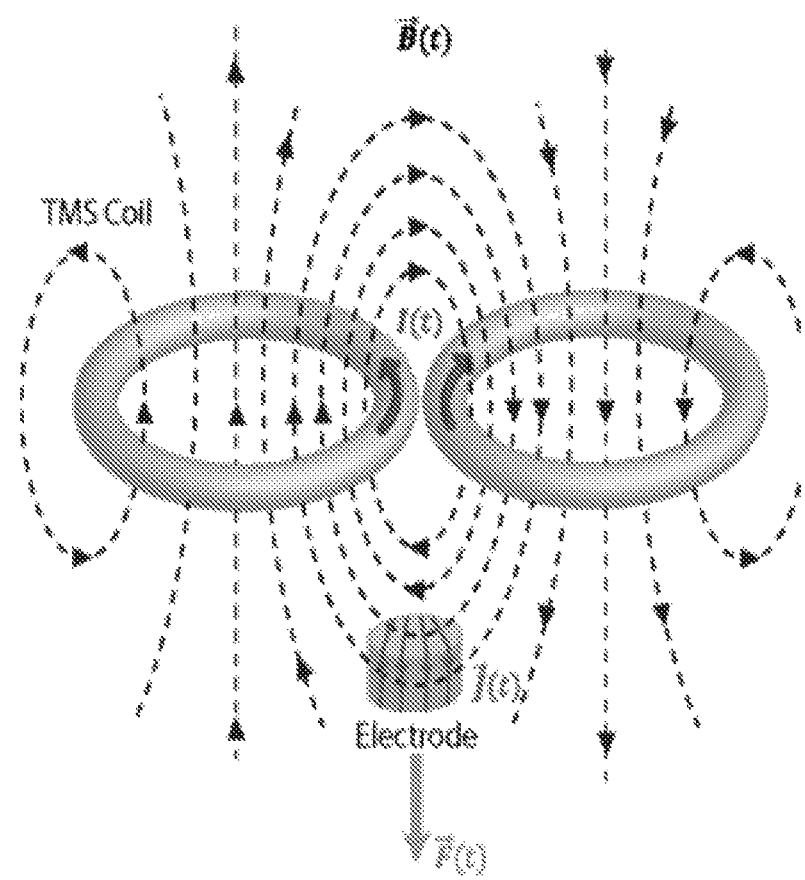
Figure 1:
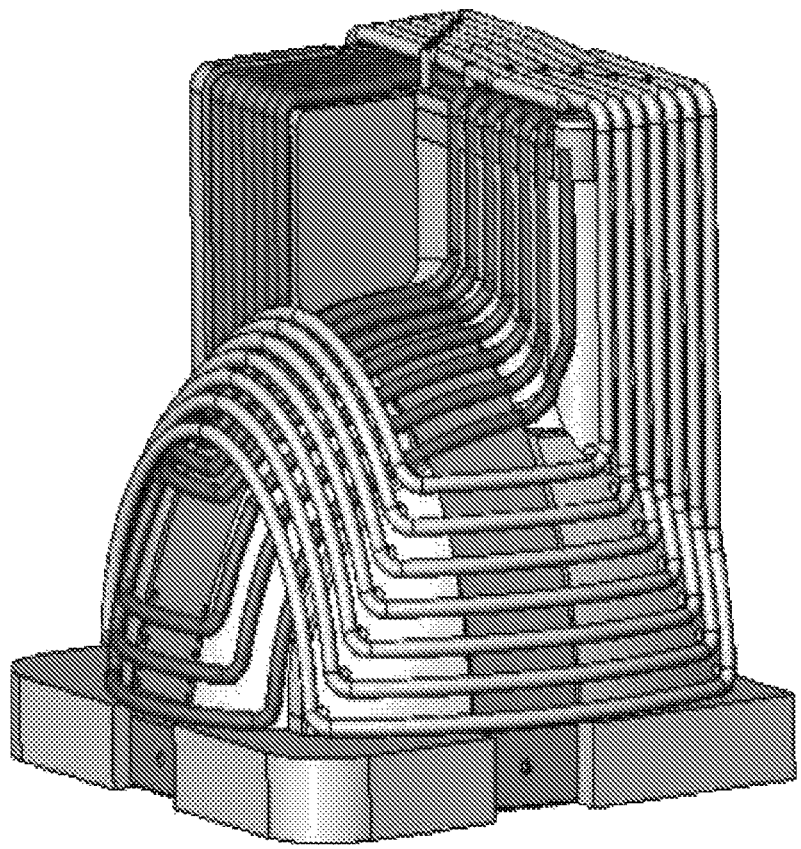

One of the shortcomings of prior art devices, such as those shown in FIG. 1, comes from the fact that the transient magnetic fields employed by such systems generate above threshold electric currents (causing neuronal firing) over large regions of the brain, and especially in the regions close to the skull. In many situations, for treatment purposes it is desirable to cause neuronal firing (i.e., achieve neuronal firing threshold) only in a certain relatively small volume deep into the brain (hereinafter referred to as "target volume") as shown by the target volume in FIG. 5. As explained herein, a magnetic stimulation system 100 configured in accordance with embodiments of the invention may be used to cause neuronal firing/stimulation only (or primarily) in the target volume.

Using the methods set forth herein, the magnetic stimulation system may be operated such that the induced currents in the target volume are larger than the currents outside the target volume. Likewise, and again using the methods set forth herein, the magnetic stimulation system may be operated such that in the target volume, currents induced by a sequence of pulses (generated from multiple pairs of coils) add up to reach the neuronal firing threshold, whereas the currents generated by the same pulses outside the target volume do not add up to the neuronal firing threshold. The magnetic stimulation system may be operated so as to achieve both the first and second situations mentioned above, thereby ensuring that neuron firing is achieved primarily in the target volume. The combination above may enable one to focus the neuronal firing in a small target volume.

The various methods (e.g. methods for achieving stimulation in a target volume) disclosed in this application may be used separately, simultaneously, or in various combinations to, by way of non-limiting example, achieve the desired stimulation of the brain.

(D). Adjusting the Conductivity of the Brain Material by the DC Magnetic Field.

The magneto-resistance phenomenon may be employed to adjust the conductivity of various regions of the brain tissue as desired. A DC magnetic field may be used to restrict the motion of charged particles and to restrict the induced currents produced by transient fields via the magneto-resistance effect. By controlling the DC magnetic field profile in space, it is possible to control the spatial distribution of the induced currents and achieve focused stimulation. Thus, the magneto-resistance effect may be used to obtain the desired stimulation location and to control the size of the stimulated region by changing the DC field distribution. Further, by adjusting the DC field distribution, it is possible to reduce the spot size and to protect high field regions near the transient coils.

Figure 5:
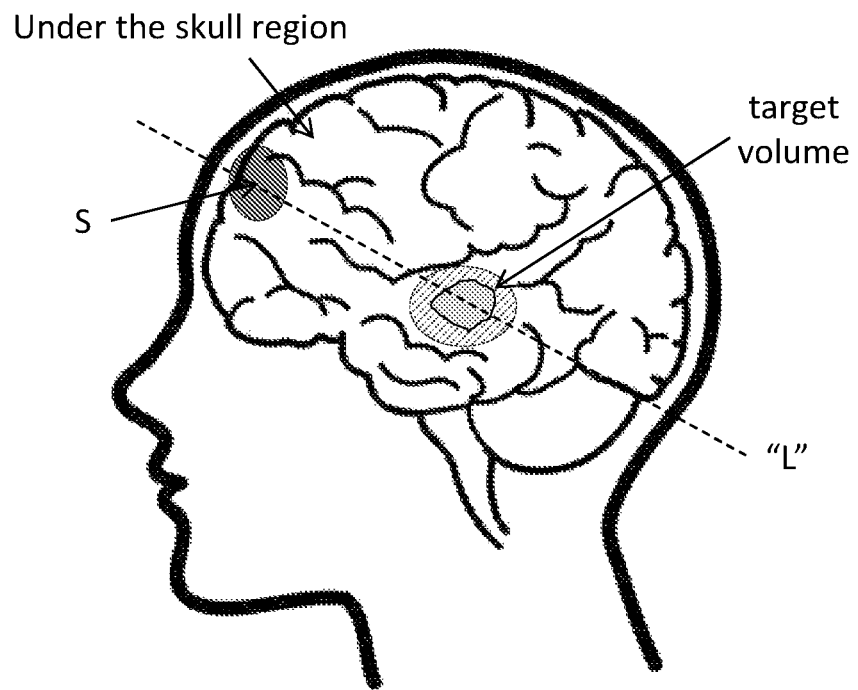
FIG. 5 shows a schematic view of a target volume inside a brain of a treatment subject according to an exemplary embodiment of the invention.

For example, with respect to FIG. 5, the distribution of the DC magnetic field may be controlled such that the transient magnetic field TF generates effective currents within the target volume "V" while the transient magnetic field TF generates significantly smaller currents in the region "S" right under the skull.

The magneto-resistance phenomenon and field dependence of magneto-conductance is shortly presented hereinafter. The ions and electrons (e.g., ions inside the brain) obey the Lorentz force equation shown below:

$$m\left(\frac{dv}{dy} + \frac{v}{\tau}\right) = -eE - evxB$$

In the above equation "m" is the mass of the ionic particle, "v" is its velocity, and "τ" is the collision mean free time. When the DC magnetic field (B) is along the z-direction, and the electric field (E), induced by the transient magnetic field (BT), is along the x-direction, then the current density related to the velocity of the particles is provided by the equations:

$$J_x = -nev_{d,x} \text{ and } J_y = -nev_{d,y} \quad J_x = \sigma_{xx}E_x \text{ and } J_y = \sigma_{yx}E_x$$

Where:

$$\sigma_{xx} = \frac{\sigma_o}{1 + \omega_c^2\tau^2} \text{ and } \sigma_{yx} = \frac{\sigma_o\omega_c\tau}{1 + \omega_c^2\tau^2}$$

$$\omega_c = \frac{eB}{m}$$

In the above equations $\omega_c$ is the cyclotron frequency and $\sigma_0$ is the tissue conductivity without a magnetic field. When the DC magnetic field increases, the tissue conductivity decreases following a $1/B^2$ dependence when B field is high. Thus, if the magnetic field is double for some regions, the conductivity will drop to ¼ times (25%). For example, with respect to FIG. 5, the distribution of the DC magnetic field may be controlled such that the DC field in the "S" volume situated right under the skull is twice as large as the DC field in the "target volume." Thus, the magneto-conductivity of the brain material in the "S" region will be about four times larger than the magnetic conductivity in the target volume V. As a result, the electric currents generated by a transient magnetic field TF into the "S" region are suppressed by the low conductivity in that region, whereas the electric currents generated by the transient magnetic field TF into the target volume V are significantly less suppressed because the conductivity in the "V" region is four times higher.

Thus, the coils of the magnetic stimulation system 100 may be operated such that a first set of coils generate a DC magnetic field having a configuration such as to adjust the conductivity of various regions of the brain tissue as desired. For example, the currents through the first set of coils may be set such that the DC magnetic field in a target volume (V) has a first value BV, whereas the DC magnetic field in the regions outside the target volume is larger than BV. As a result, the conductivity of the brain matter inside the target volume (V) is smaller than the conductivity of the brain matter outside the target volume. Further, at the same time with the first set of coils generating the above mentioned DC field, in accordance with certain aspects of an embodiment, transient currents may be driven through a second set of coils of the magnetic stimulator 100 such as to generate transient magnetic fields TF into the brain. The transient magnetic fields TF induce currents into the brain matter (by magnetic induction: ∇×E=−dB/dT). The induced currents depend both on the electromagnetic induction and on the conductivity of the particular brain region. The conductivity of the brain regions is adjusted by the DC field configuration such that the currents induced by the transient magnetic fields inside the target volume "V" are large enough to reach neuronal firing threshold (thereby causing neuronal firing), whereas the currents induced outside the volume are not large enough to reach neuronal firing threshold (thereby not causing neuronal firing).

Figure 6:
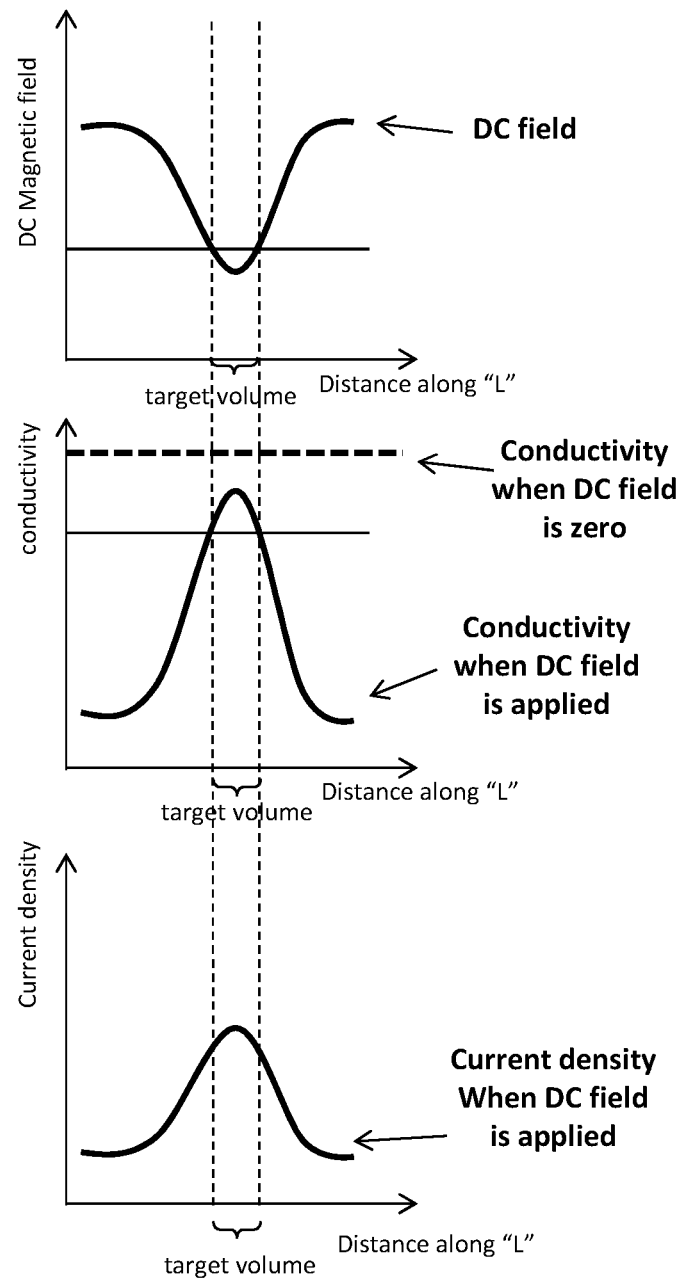
FIG. 6 shows schematically the distributions of the DC magnetic field, the conductivity, and the current density along the line "L" in FIG. 5 passing through the brain of a subject and through the target volume according to an exemplary embodiment of the invention.

The above described behavior of brain conductivities and induced currents as a function of the DC fields applied is explained with reference to FIG. 6 of the drawings. FIG. 6 shows schematically the distributions of the DC magnetic field, the conductivity, and the current density along the line "L" in FIG. 5 passing through the brain of a subject and through the target volume. As seen in FIG. 6, the brain conductivities and the induced currents are higher in the region where the DC field is low, such as inside the target volume V. Conversely, the brain conductivities and the induced currents are smaller in the region where the DC field is high, such as in the regions outside of the target volume V.

Figure 7:
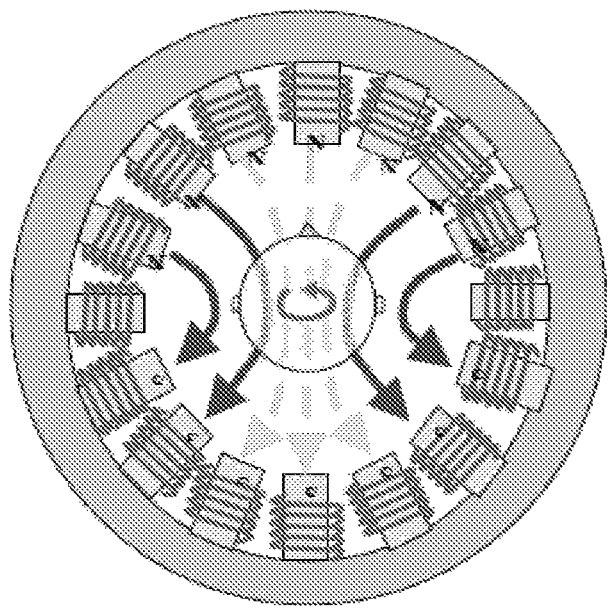
FIG. 7 shows schematically the distributions of the magnetic field generated by the magnetic stimulator system during a first time period according to an exemplary embodiment of the invention.
Figure 8:
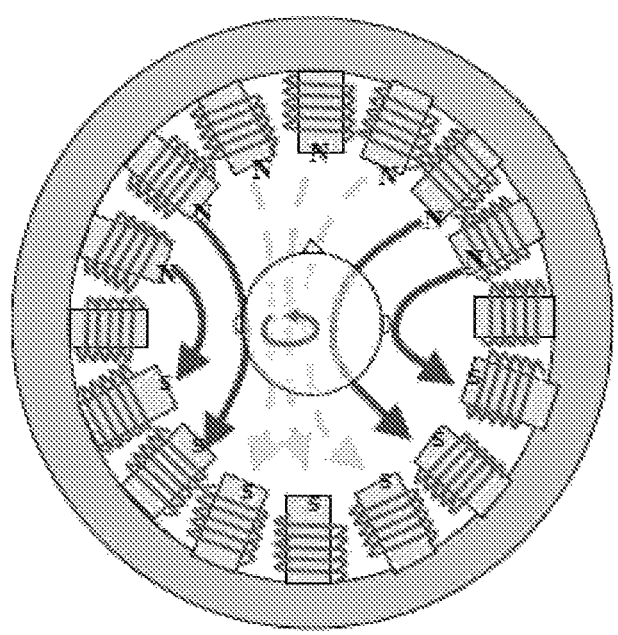
FIG. 8 shows schematically the distributions of the magnetic field generated by the magnetic stimulator system during another time period according to an exemplary embodiment of the invention.

The configuration of the DC and transient magnetic fields may be changed (e.g., continuously) during the treatment, which in turn changes the conductivity distribution and the pattern of induced currents in the brain, thereby changing the stimulated brain region. For example, during a first time period, a first DC field may be applied (e.g., as shown in FIG. 7), which may induce the desired currents in the target volume V1 and restrict the induced currents outside the volume V1. During a second period, a second DC and transient field may be applied (e.g., as shown in FIG. 8), which may induce the desired current in another target volume V2 but will restrict currents to be induced by transient field outside the volume V2. During the treatment period, both the DC and transient field configurations can be adjusted (e.g., together or separately) such that the target volume is moved inside the brain, thereby moving the brain region to which magnetic stimulation treatment is applied.

This way, the target volume to which treatment is delivered can be moved from one region to another inside the brain without moving the patient.

The DC and transient fields may be adjusted such that the target volume "V" may have a diameter as small as 5 mm. The DC fields and the transient fields may be adjusted such that the target volume "V" may have a diameter smaller than 5 mm, or smaller than 10 mm, or smaller than 15 mm, or smaller than 20 mm, or smaller than 30 mm. The target volume may be smaller than 5% of the brain volume, smaller than 10% of the brain volume, smaller than 20% of the brain volume, or smaller than 30% of the brain volume. The DC fields and the transient fields may be adjusted such that the target volume "V" may be as deep as 10 mm, 20 mm, 30 mm, 50 mm, 60 mm or 100 mm under the surface of the brain. The depth can be more than 100 mm when applied to other body parts or objects.

The DC magnetic field in the target volume "V" may be from about 0.001 Tesla to about 0.5 Tesla. The DC magnetic field at the surface of the head (in the air just outside of the surface of the magnet core) may be from about 1 Tesla to about 7 Tesla.

The transient magnetic fields may have the following characteristics. The transient magnetic fields may be such that, in the target volume, dB/dt is between $10^4$ and $10^5$ Tesla per second. The transient magnetic fields may be such that, at the surface of the head, dB/dt is between $2 \times 10^4$ and $2 \times 10^5$ Tesla per second. The transient fields may come as pulses or sequences of pulses. The pulses may last between a few microseconds and 0.5 ms. The pulse sequences may include pulses spaced apart at less than 0.1 ms, or less than 0.05 ms, or less than 0.02 ms, or about 0.01 ms. The pulse sequences may include pulses spaced apart at less than about 1 ms, 10 ms, or 1000 ms.

The number of coils (poles) can range from a few coils to several hundreds to even thousands of coils. It is likely that coils numbering within the range of dozens to 200 will be suitable for use with the current technology. The ranges of values for the DC ramp up peak current is ~100-1000 A and the pulse peak current is ~200-4000 A, although higher and lower values can be used. The transient field coils of the stimulator system 100 may be driven in pairs such that one coil corresponds to a north pole and the other to a south pole.

(E). Summation of the Effects of Sequences of Magnetic Pulses and Magnetic Field Beams.

Experimental studies performed by the inventors herein have shown a summation effect of sub-threshold behavior for the Transcranial Magnetic Stimulation applied to the human motor cortex for generating motor response. The above experimental studies have been described in detail in the article "Neural Summation in Human Motor Cortex by Subthreshold Transcranial Magnetic Stimulations" (Xiaoming Du, Fow-Sen Choa, Ann Summerfelt, Malle A. Tagamets, Laura M. Rowland, Peter Kochunov, Paul Shepard, L. Elliot Hong; published in Experimental Brain Research, DOI 10.1007/s00221-014-4146-z, November 2014) incorporated hereinafter in its entirety as if fully set forth herein.

Sub-threshold stimulation is a stimulation that is not strong enough to generate action potential or motor response. The inventors showed that when two sub-threshold stimuli are fired in close temporal proximity, a motor response can be generated. Therefore, it is possible to use sub-threshold firing to avoid neuromodulation taking place outside of desired regions. Only when multiple sub-threshold stimulations converge at the desired region will an action potential or above threshold firing of the neural tissue at that location take place.

Figure 9:
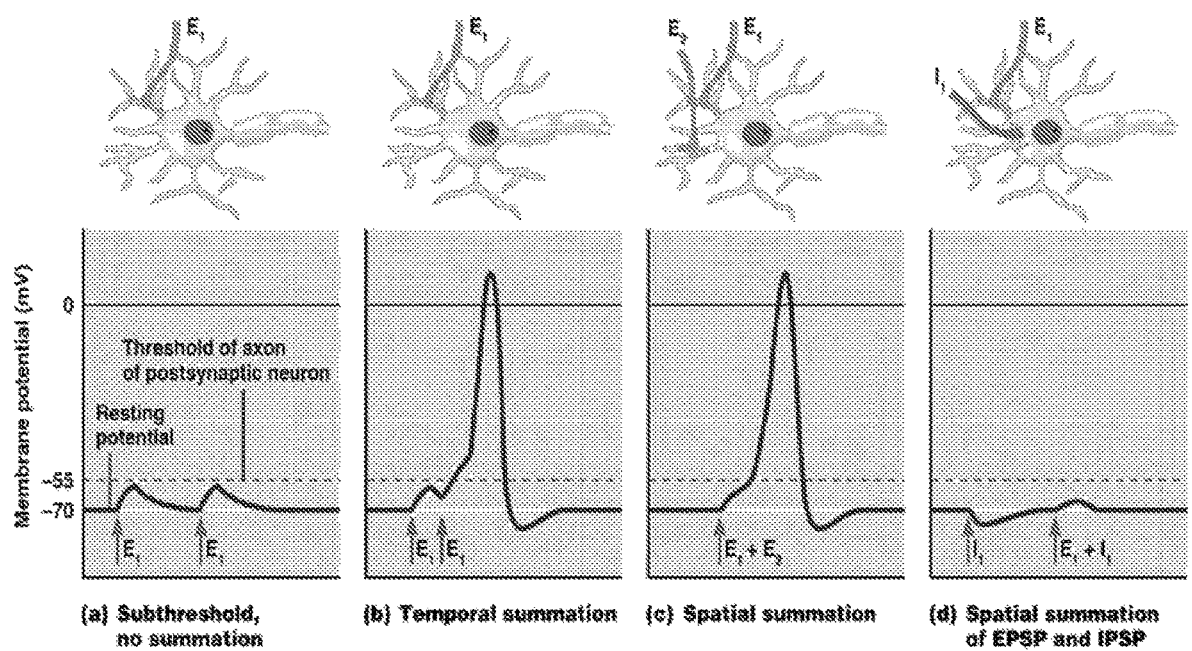
FIGS. 9(a) to (d) show schematically four neuron stimulation circumstances according to an exemplary embodiment of the invention.

Some aspects of the invention include the summation of two or more sub-threshold stimulations in order to achieve neuron firing. Stimulation summation may be achieved by exposing the target to two or more sub-threshold stimulations. The sub-threshold stimulations may be released within a certain window of time (temporal), as shown in FIG. 9(*b*), or they may occur at the same time but reach the neuron from a different path (spatial), as shown in FIG. 9(*c*). Inhibitory postsynaptic potentials (IPSP) may also be combined with excitatory postsynaptic potentials (EPSP) to prevent neuron firing, as shown in FIG. 9(*d*). The membrane potential of a neuron weakens over time, such that sub-threshold stimulations must be released within a certain period of time when using temporal summation, as shown in FIG. 9(*a*). By sequentially sending transient pulses with different spatial paths, at different times, the time summation effect achieves neuron activation in a very small target region while tissues outside the highest overlapping area are well protected and remain below stimulation activation.

TABLE 1

| Delays | | 1 ms | 2 ms | 5 ms | 10 ms |
|---|---|---|---|---|---|
| | Two pulses with 10% below threshold intensity | | | | |
| Run 1 EMG | | 13.03 | 1642.27 | 459.70 | 28.73 |
| | Two pulses with 20% below threshold intensity | | | | |
| Run 2 EMG | | 8.43 | 65.60 | 221.11 | 5.26 | 1.37 |

Table 1 depicts experimental results on temporal summation for pulses that are 10% and 20% below the threshold intensity. The table shows time constant neurons can hold sub-threshold stimulation in the range of milliseconds to tens of milliseconds which is well within the range of the present invention. The sample two-dimensional unit described above confirmed that summation does occur.

Neural firing threshold can be achieved directly, that is by generating pulses of current above the threshold. Neural firing threshold can also be achieved indirectly by the summation of multiple sub-threshold field stimulations (and the induced voltages and currents) ordered in time. Neural stimulation/firing can be achieved by sequentially generating multiple lines of induced currents and only allowing the cross point of these lines to accumulate sufficient charge on the cell membrane.

For example, assume that a sequence of time-ordered magnetic field pulses P1 to P10 is applied to a neuron cell in the brain. Each of the P1 to P10 generates an induced current that leads to an increase of the membrane voltage by $\Delta V = C * \Delta Q$, where C is membrane capacitance, thereby inducing a charge $\Delta Q$ on the membrane. The voltage $\Delta V$ and the charge $\Delta Q$ generated by a single pulse, out of the pulses P1 to P10, is not enough to depolarize the membrane, reach action potential threshold, or reach neural firing threshold. However, if the pulses in the sequence are spaced apart such as to allow cross-point summation between the pulses, the voltages generated by each of the pulses may add up in time such that, after a number of pulses, $\Delta V$ of the membrane will be large enough to depolarize the membrane and reach action potential thresholds. Thus, firing threshold can be obtained by the summation of multiple sub-threshold stimulations.

As explained in the following with reference to FIG. 10, by using a sequence of time-ordered sub-threshold pulses, it is possible to achieve targeted neural stimulation in a small volume at any desired depth into the brain.

Figure 10:
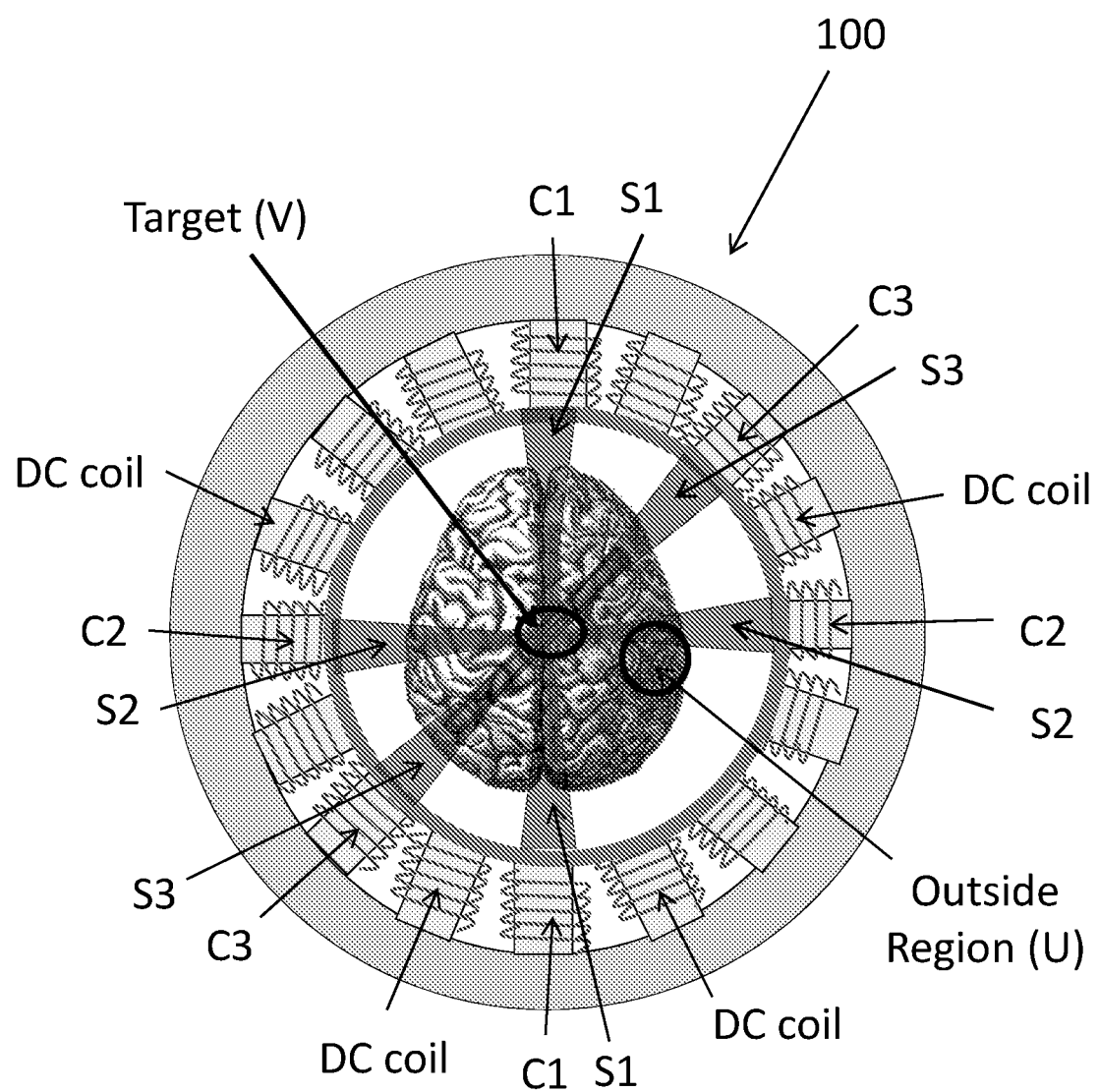
FIG. 10 shows a schematic view of a magnetic stimulator system and a method for running such system according to an exemplary embodiment of the invention.

The magnetic stimulation system 100, as shown in FIG. 10, may be operated such that in the target volume, currents induced by a sequence of pulses (generated from multiple pairs of coils) add up to reach neural firing threshold, whereas the currents generated by the same pulses outside the target volume do not add up to the neural firing threshold. The coils may be driven in pairs such that one coil corresponds to a north pole and the other to a south pole.

For example, a sequence of transient magnetic pulses may be fired from a pair of coils of the stimulation system 100, as shown in FIG. 10, as follows: a first transient pulse P1 is fired from the pair of coils C1 at the time t1; a second transient pulse P2 is fired from the pair of coils C2 at the time t2=t1+dT; and a third transient pulse P3 is fired from the pair of coils C3 at the time t3=t1+2*dT. Each of the transient pulses may have a pulse length "tp" (which may be from about 10 microseconds to about 1 ms) which is shorter than the time between pulses dT (which may be from about 1 ms to about 100 ms). The pulses P1, P2 and P3 have a sub-threshold strength which is 60% or more of the threshold strength.

Pulse P1 generates a magnetic field B1 having a specific distribution B1(x, y, z). The distribution B1(x, y, z) is such as to form a beam S1 for which the magnetic field B1 is larger in the region of the beam S1 and smaller in the regions outside the beam S1 (e.g., the field outside the region S1 is sub-threshold). Similarly, pulse P2 generates a magnetic field B2 having a specific distribution B2(x, y, z). The distribution B2(x, y, z) is such as to form a beam S2 for which the magnetic field B2 is larger in the region of the beam S2 and smaller in the regions outside the beam S2 (e.g., the field outside the region S2 is sub-threshold). Further, pulse P3 generates a magnetic field B3 having a specific distribution B3(x, y, z). The distribution B3(x, y, z) is such as to form a beam S3 for which the magnetic field B3 is larger in the region of the beam S3 and smaller in the regions outside the beam S3 (e.g., the field outside the region S3 is sub-threshold).

The stimulator system 100 may be positioned and/or moved such that the target volume V is at the intersection of the beams S1, S2, and S3.

The brain material situated at the intersection of beams S1, S2, and S3 (inside the target volume V), receives a sequence of three pulses (i.e., P1, P2 and P3), each having a strength that is, for example, 60% of the threshold strength. Thus, even though none of the three pulses has enough strength to cause stimulation, the effects of the pulses P1, P2, and P3 (all of them being 60% of the threshold strength) may add up so as to cause neuron firing.

At the same time, the brain material outside the intersection of beams S1, S2, and S3 (e.g., the region "U" outside of the target volume) receives a sequence of magnetic pulses (corresponding to the three pulses P1, P2, and P3), but the magnetic field generated by the pulses P1, P2, and P3 in this outside region "U" is less than 60% (or at least one of the pulses has a strength less than 60%) of the threshold strength. As a result, in the region outside V (e.g., in region U), the magnetic fields corresponding to the three pulses do not add up to a composite strength above the threshold and, consequently, the neurons outside of the volume V will not fire.

In other words, the nerve cells along the transient magnetic field path (but not situated at the intersection of beams S1 to S3) will never be able to accumulate sufficient charge to depolarize their membrane and reach action potential threshold. However, the nerve cells at the cross point (situated at the intersection of beams S1, S2, and S3) can accumulate shots from different paths and eventually accumulate sufficient charges to depolarize the membrane and reach action potential. By doing so, equivalent magnetic focusing is achieved through superposition of coil arrays and summation of different paths.

While the above example has been explained with respect to a sequence of three pulses having strengths larger than 60%, the skilled artisan would understand that a sequence of pulses including any number of pulses may be used (e.g., 5, 10, 15, 20, 100, 500 pulses) and the pulse strengths may have various values (e.g., 1%, 10%, 50%, 70%, 80% of the threshold strength). Further, the time spacing (dT), the pulse length (tp) of the pulse sequences, and the pulse shapes may be adjusted such as to trigger neuronal firing in the desired target volume while at the same time preventing the triggering of neuronal firing in other brain regions.

(F). Focusing the Pulsed Transient Magnetic Fields into the Target Volume by Superposition of Magnetic Fields Generated by a Plurality of Pairs of Coils.

As mentioned above, the magnetic stimulation system 100 includes a plurality of coils that may be powered such as to generate a pulsed transient magnetic field by driving a transient current through the coils. The coils may be driven in pairs such that one coil corresponds to a north pole and the other to a south pole.

The inventors herein have discovered that the transient magnetic field in a certain volume inside the coil system 100 may be focused by superimposing the magnetic fields of various coil pairs of the system 100. Further, the inventors herein have discovered a near-field effect in the sense that the composite field profile becomes smaller with decreasing the coil diameter, and the field spot size is reduced when the coil diameter is reduced. The smaller the diameter of the coils and the smaller the inter-coils spacing (and the larger the density of coils in the array), the smaller the field spot size and the composite field profile. Moreover, the inventors herein have discovered that the field spot size can be reduced by using diagonal superposition of pulsed magnetic fields from array pairs and near-field geometric effects.

All of the above enable the operator of the magnetic stimulator to obtain a highly focused magnetic field with a spot size smaller than a few mm in diameter.

Figure 11:
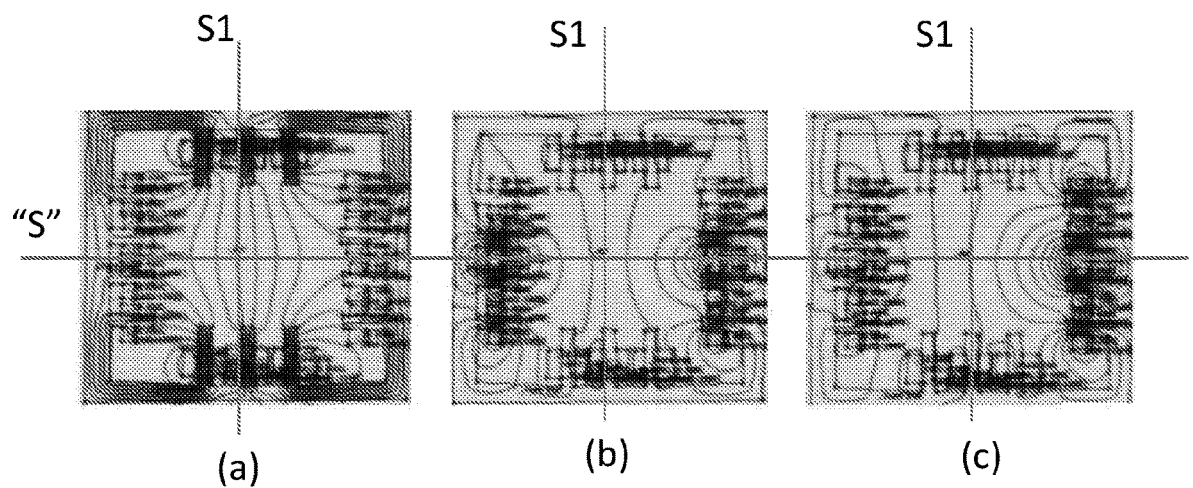
FIGS. 11 (a) to (c) show a schematic view of simulation results for a configuration of a magnetic field for a two-dimensional system according to an exemplary embodiment of the invention.

FIGS. 11(a)-(c) show simulation results of a two-dimensional design. FIG. 11(a) shows that the relative magnetic field spreads everywhere when the left and right DC control field is not turned on. FIG. 11(b) shows a case when the left and right DC magnetic fields are turned on and, as a result, the pulsed field becomes focused and can only pass through the middle part of the region. The focal point of the field may be moved from one location to another by adjusting the DC magnetic fields of the surrounding coil pairs. This way, the focal point may be shifted left and right or forward and backwards as shown in FIG. 11(c). In the 3-D case, a similar method may be used to adjust the location of the focal point. Alternatively, the whole two dimensional unit may be moved up and down to adjust the focal point in the z-direction. Because more DC coils may be distributed in a 3-D space, multiple field paths may be obtained and the paths may be nonlinear, thus further increasing the ability to localize and to focus.

Figure 12:
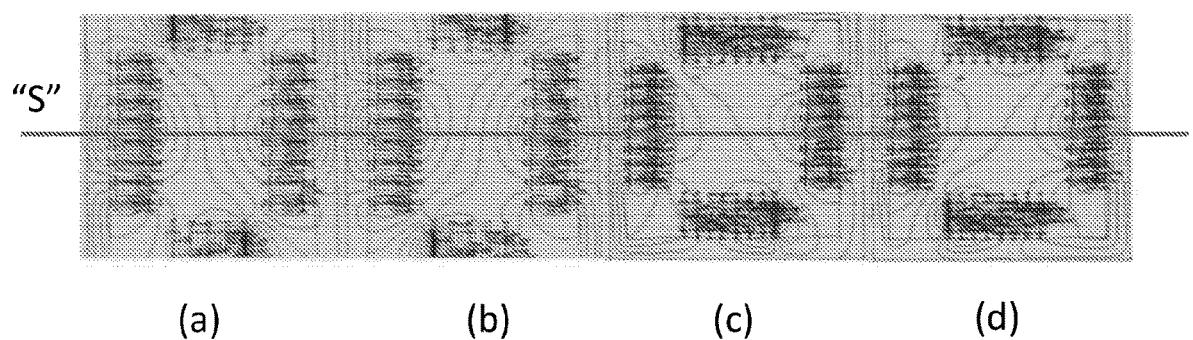
FIGS. 12 (a) to (d) show a schematic view of simulation results for a configuration of a magnetic field in a magnetic system according to an exemplary embodiment of the invention.

FIG. 12 shows that the required DC current to achieve focusing may be reduced by increasing the coil/pole number, reducing the pole diameter of the coils, and operating on diagonal poles (shut off the rest). In the example setup depicted in FIG. 11, the required DC current is over 1 kA in order to achieve focusing. In the FIG. 12 setup, the required DC current is reduced down to 400 A.

To greatly reduce the focal spot size, the pole diameter may be reduced and the pole number may be increased as shown in FIGS. 12 (c) and (d). By sequentially turning on the transient field in cross diagonal paths, the cross point volume can be very small. The volume of the above threshold region may be further reduced down to theoretically infinitely small by appropriately adjusting the transient field strength of each path.

FIGS. 13 (a) and (b) show computer simulation results for the magnetic field shape generated by a system of eight pairs of coils. FIG. 13(a) shows the distribution of the magnetic field lines. FIG. 13(b) shows the magnitude of the magnetic field as a function of position along the line "S" in FIG. 13(a). As seen in FIG. 13(b), the value of the magnetic field exhibits a pronounced peak (relatively small FWHM) in the central region, which proves the focusing effect of the multi-coil system in FIG. 13(a).

FIG. 14(a) shows a magnetic stimulation system 100 according to certain aspects of an exemplary embodiment of the invention. The magnetic stimulation system 100 may further include magnetic shields (e.g., the shields 145 in FIG. 14(a)) to further adjust the magnetic field distribution generated by the stimulation system (e.g., inside the brain of the patient), thereby improving the focus/shape of the transient or DC magnetic fields as shown by FIG. 14(a). Magnetic shields 145 include nonmagnetic materials having high electrical conductivity (e.g. graphene, silver, copper, etc.).

FIG. 14(b) shows exemplary configurations of the magnetic shields (e.g. 141 and 142) and their effect on an applied external magnetic field. The two magnetic shields 141 and 142 may have a ring or disk shape. The induced eddy currents into the shields may provide a counter magnetic field in an opposite direction to the externally applied forward magnetic field. The summation of the forward and counter magnetic fields creates a total field distribution that redistributes the externally applied field to a distorted but more focused field distribution (as shown in the left side of FIG. 14(b)). The shape of the total final field may be determined by treating the inserted high conductivity shield material as boundary conditions for the original field source and by solving the field equation with these boundary conditions.

The solution of such an equation shows a more focused field distribution as shown by the field in the right panel of FIG. 14(b).

(G) Reducing the Duty Cycle for the DC Current

Figure 15:
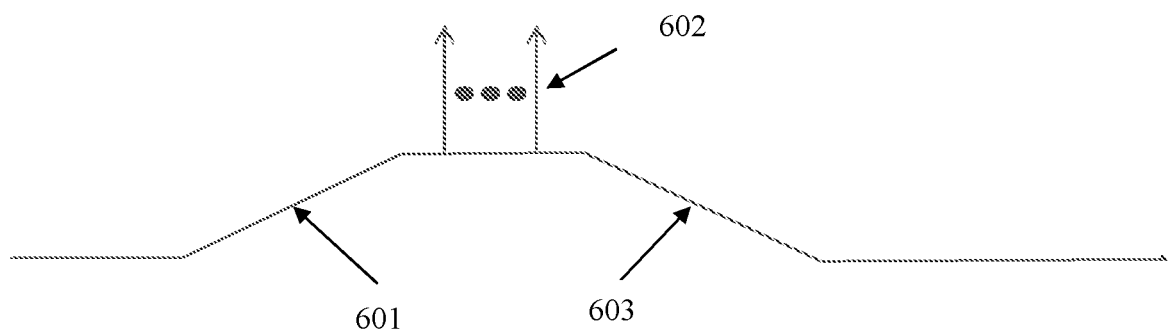
FIG. 15 shows a schematic view of a method of applying DC current to coils of a stimulator system according to an exemplary embodiment of the invention.

The equivalent DC current may be further reduced by reducing its duty cycle, as depicted in FIG. 15. This method employs a slow DC field ramp up 601, followed by multiple transient AC pulses 602, followed by a ramp down of the DC current back to the original stage 603. This process will reduce heat and magnetic stress of the operation.

(H). Configuration of the Control System

Figure 16:
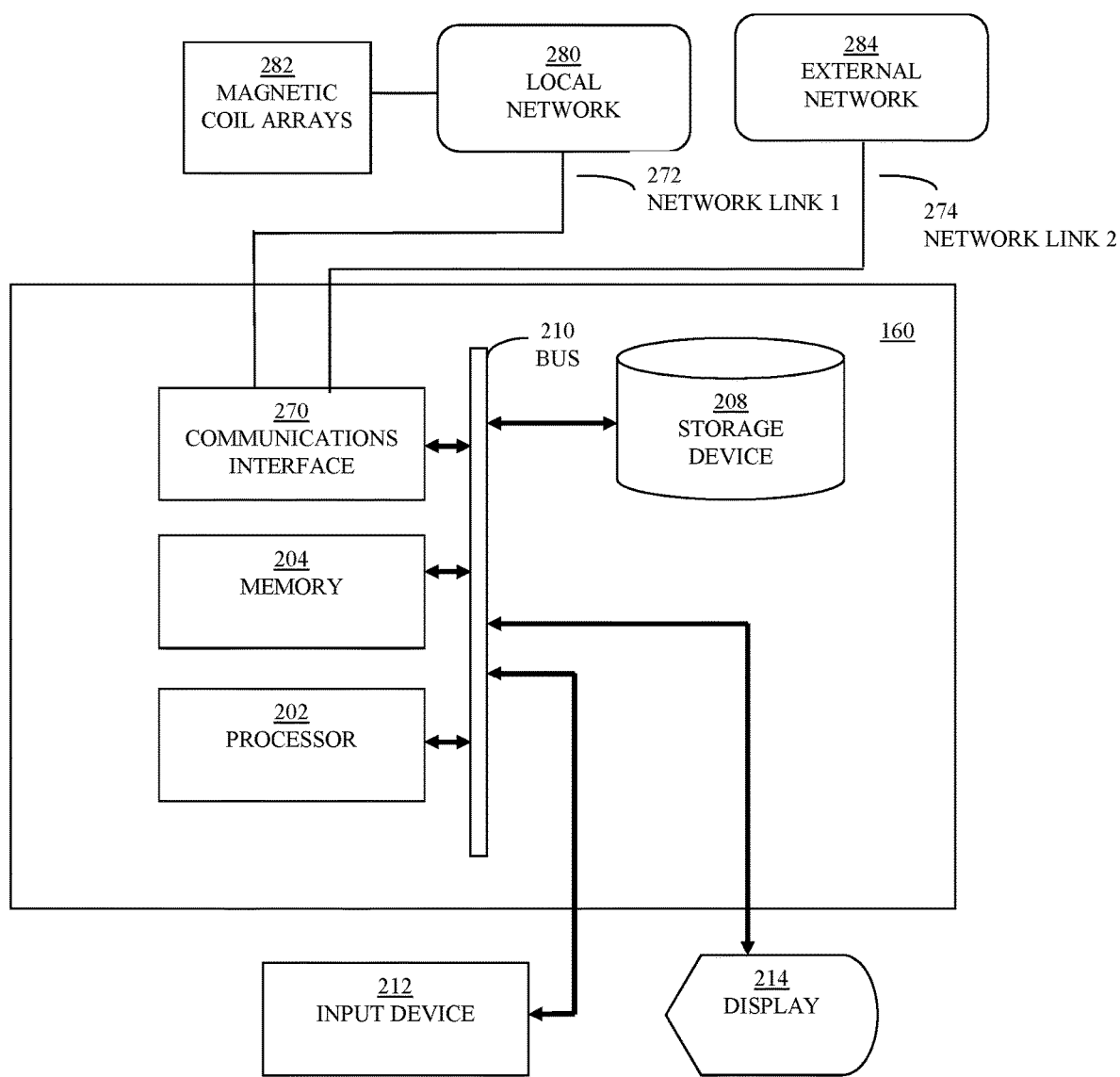
FIG. 16 shows a schematic view of a control system according to an exemplary embodiment of the invention.

FIG. 16 illustrates an example control system 160. The control system comprises a processor 202, memory 204, storage device 208, bus 210, input device 212, display 214, and communications interface 270. Control system 160 may be an individual system, as shown in FIG. 16, or it may be integrated into another medical system or computer.

Input device 212 allows for patient specific treatment plans to be uploaded into the system. In some instances, the input device includes a keyboard, mouse, touchscreen, or other interface to allow for operator control. The input device may include algorithms to calculate a treatment plan. These interfaces, along with display 214, allow the operator to enter or perform calculation of a treatment plan or make changes to an uploaded plan. Preplanned patient-specific treatment plans may also be uploaded through communications interface 270. Files may be uploaded from an external computer network (e.g., the Internet) 284 via network link 2, 274 or from a local network via network link 1, 272. Communications interface 270 also communicates with magnetic coil array 282. Instructions are sent to the magnetic coil arrays to execute the treatment plan. Input device 212 can generate individualized, computer-generated treatment plans. The treatment plan can then be executed through the computerized controls for the DC coils and transient coils using computer assisted algorithms.

The controls can include turning on and off particular configurations of the number of coils, the spatial locations of the coils, the different intensities among the coils, and the different timing and patterns of the individual coils. The computerized treatment solutions can be anatomically guided by the actual images of the structure of the body parts of the patient or participant. The anatomic images can be from magnetic resonance imaging or other recording devices. The anatomic images are input into the computers. The computer will then calculate and output the DC fields and path needed for the treatment plan, and create the sequence for turning on and off particular configurations on the number of coils, the spatial locations of the coils, the different intensities among the coils, and the different timing and patterns of the individual coils. Similarly, the device can output and execute the precise locations and strength of the magnetic fields.

(I). Methods and Devices for Controlling the Configuration of Magnetic Fields

In accordance with certain aspects of an embodiment, the magnetic stimulators may have various coil structures and configurations as described in the following. Exemplary embodiments may include active coil elements and passive shields (alone or in combination) in order to obtain a desired composite field distribution, which composite field distribution may (by way of non-limiting example) achieve a magnetic field distribution having a hole, or achieve a magnetic field distribution having a concentrated spot of magnetic field, or such other field shapes as may occur to those skilled in the art. For both configurations employing active coil arrays and configurations employing a passive shield, Fourier analysis principles may be used to select appropriate Fourier components in the spatial domain such as to reduce the size of the hole or the size of the focal spot. In order to obtain a very small diameter hole or focused spot size, the diameters of the coil elements or the shield disks also have to be small.

Figure 17:
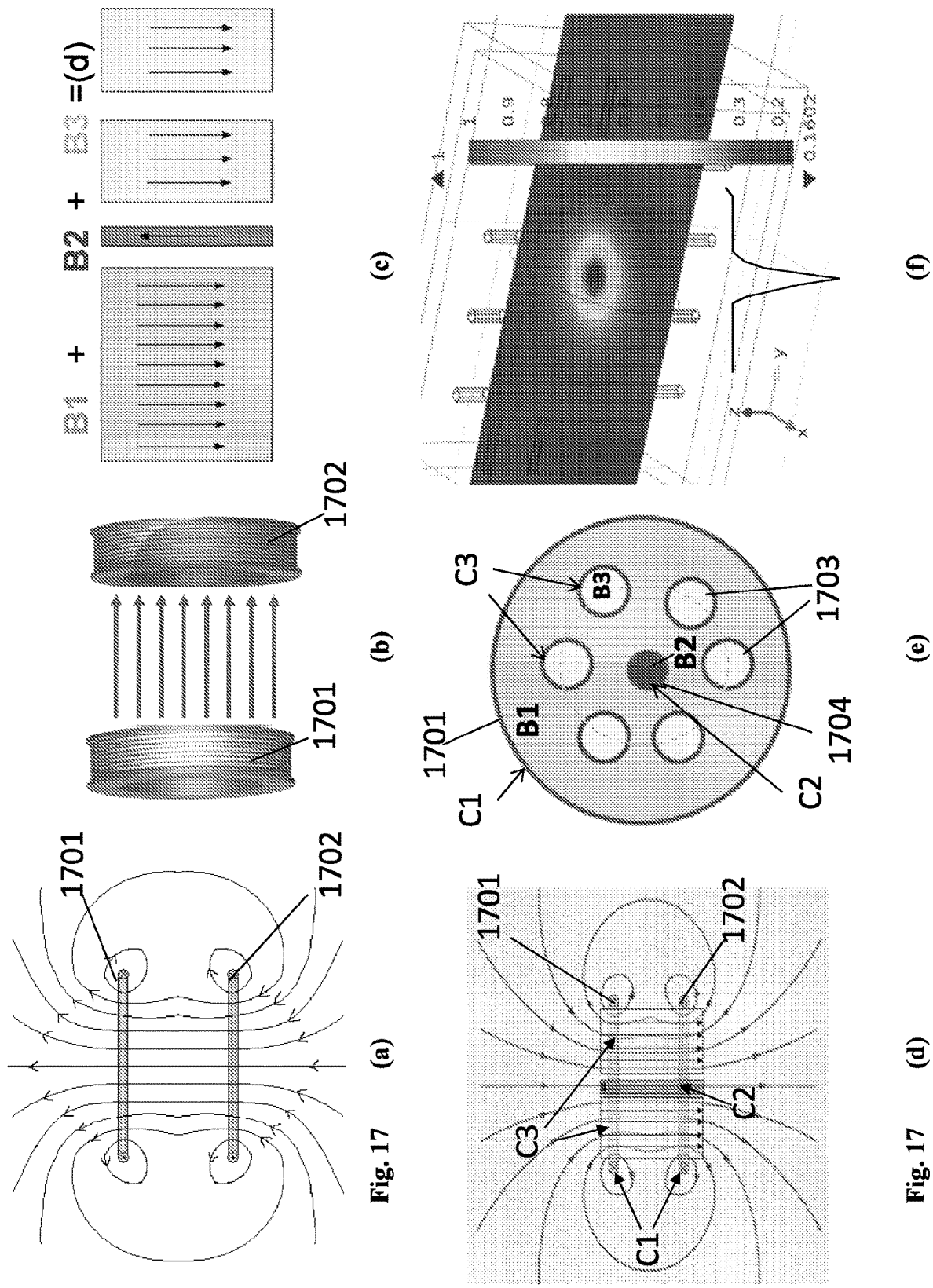
FIGS. 17(a)-(f) show a system for generating a magnetic hole within a target volume in a patient's body in accordance with certain aspects of an embodiment of the invention. More particularly, FIGS. 17 (a) and (b) show the generation of a uniform magnetic field by a pair of current loops or coils.

FIGS. 17 (a) and (b) schematically depict exemplary methods of generating a uniform magnetic field by using a pair of current loops or coils 1701 and 1702. A magnetic field distribution having a hole (as shown in FIG. 17(f) and discussed in more detail below) may be created by using field superposition as conceptually shown in FIG. 17(c). A field superposition may be obtained by adding the uniform B-field distribution (marked B1), which may be formed by coils 1701 and 1702, with a reverse direction field produced by a smaller diameter coil pair (marked B2) and with a field generated by an array of coil pairs surrounding the small diameter coil pair (marked B3). This field distribution may be obtained by the coil configuration shown by FIGS. 17(d)-(e) (FIG. 17 (d) shows a side view of such configuration and FIG. 17(e) shows a top down view of such configuration), in which smaller diameter coil pair 1704 is centrally positioned within coils 1701 and 1702, and array of coil pairs 1703 is situated between smaller diameter coil pair 1704 and coils 1701 and 1702.

The coil configuration shown by FIGS. 17(d)-(e) includes pair of coils 1701 and 1702 generating the field distribution B1, a pair of coils 1704 generating the field B2, and pairs of coils 1703 generating the field B3. The total field distribution generated by the configurations of coils 1701/1702, 1703 and 1704 is given by the superposition of field distributions B1, B2, and B3.

The coil configuration shown by FIGS. 17 (d)-(e) can achieve a magnetic field distribution having a hole as shown in FIG. 17(f). The magnetic field (B3) in FIG. 17(c) is used to compensate for the fringes created by the small diameter coil pair 1704. By adjusting amplitudes of the 3 different spatial Fourier components (i.e., coil pairs 1701/1702, 1703 and 1704) we can obtain a "hole" with sharp change of magnetic field distribution. FIG. 17 (f) shows the field distribution, obtained by computer simulation, for such a coil configuration (FIG. 17(f) is color coded where the red color represents strong magnetic field and blue represents weak magnetic field).

Figure 18:
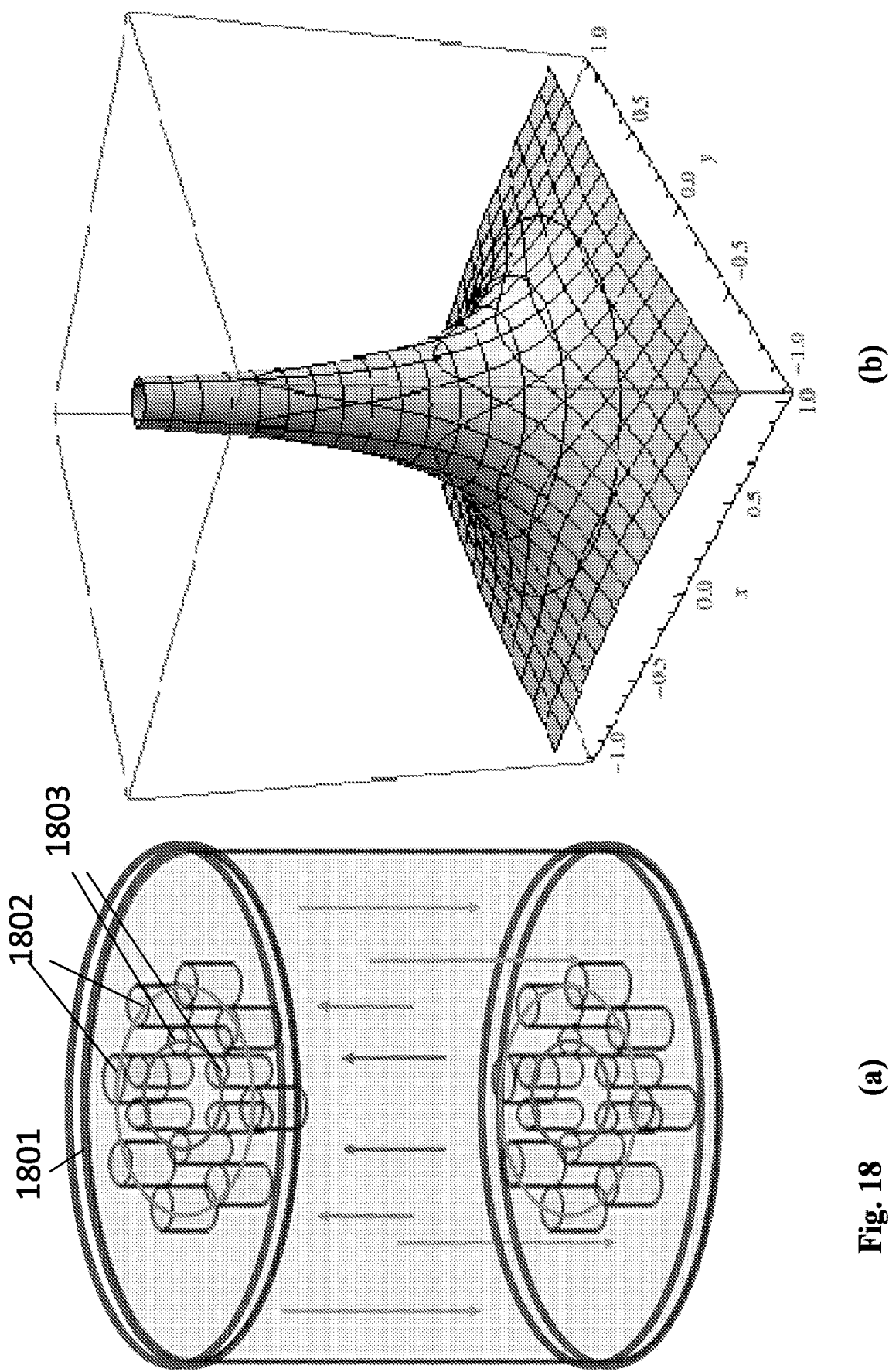
FIG. 18(a) shows a coil array structure and superposition of 3 different field distributions to form a focused field, which focused field is shown in FIG. 18(b).

A similarly arranged coil configuration can also create a field distribution having a focus spot where the magnetic field is higher. A focus spot may be obtained by arranging spatial Fourier components as shown in FIG. 18 (similar to the way a hole is created by the coil configuration shown in FIGS. 17(d)-(e)), including a first coil pair 1801, an array of second coil pairs 1802 positioned within the circumference of first coil pair 1801, and an array of third coil pairs 1803 positioned within the array of second coil pairs 1802, all as shown in the exemplary embodiment of such a coil array structure arrangement in FIG. 18(a). The amplitudes of spatial Fourier components can be arranged in the three different types of field distributions so as to form a focused field distribution as shown in FIG. 18(b).

Figure 19A:
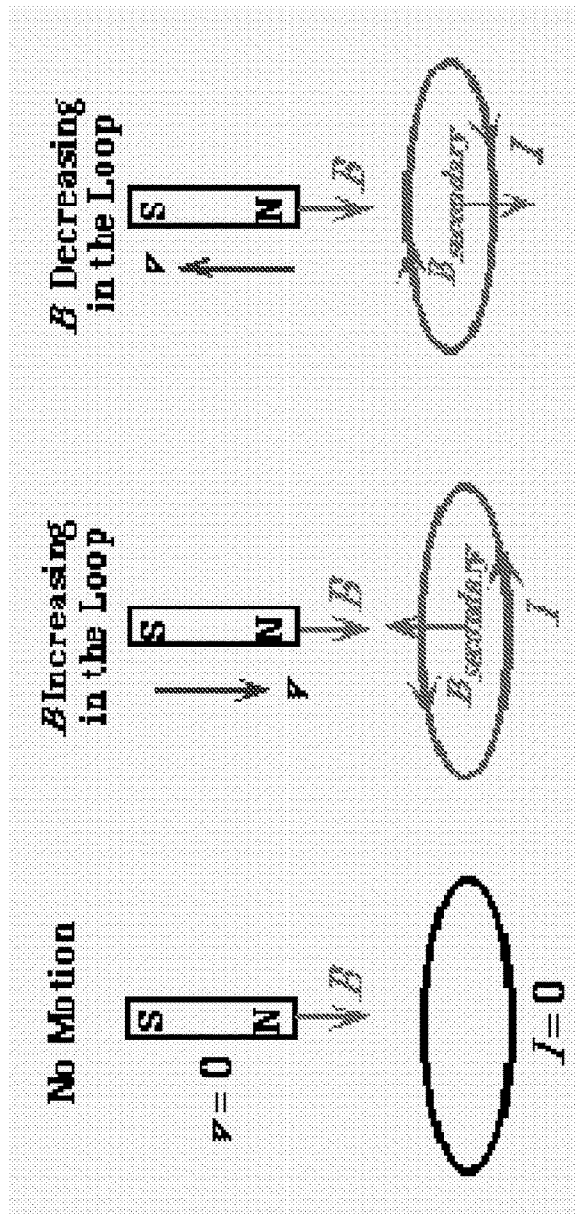
FIG. 19 (a) shows a schematic view of induced current in a conductive wire.
FIG. 19(b) shows a schematic view of induced current in a conductive plate to create a shield for a transient magnetic field.
Figure 19:
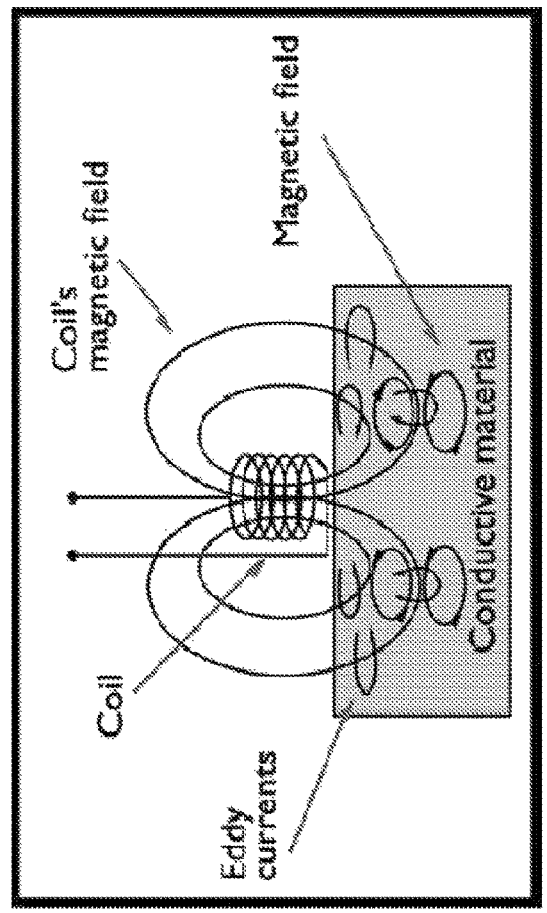
Figure 22B:
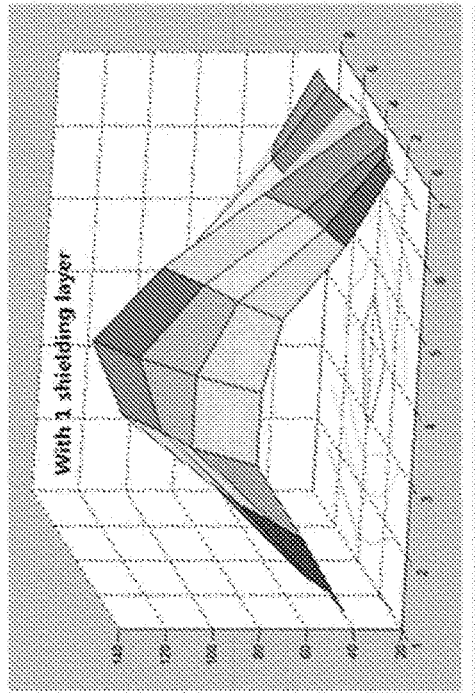
FIG. 22(b) shows field distribution with one layer shielding.
Figure 22D:
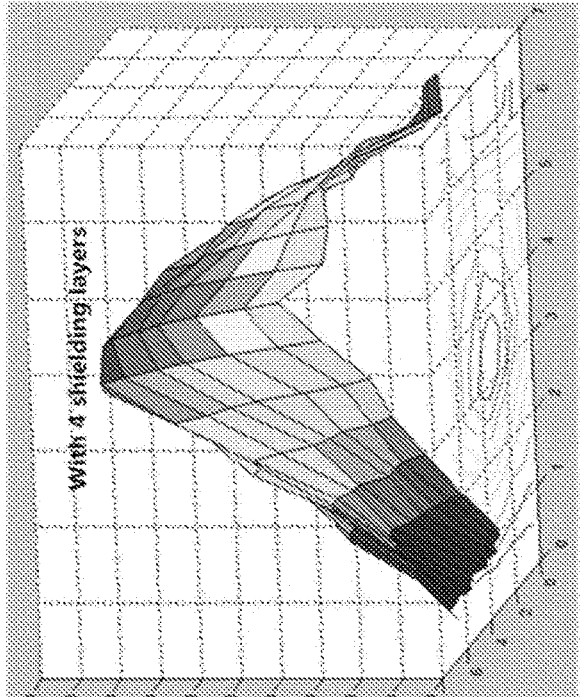
FIG. 22(d) shows field distribution with 4 layers of shielding.
Figure 22A:
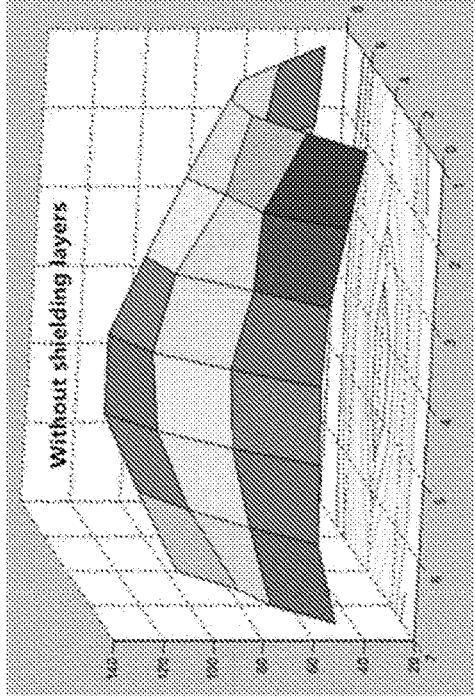
FIG. 22(a) shows measured electric field strength distribution without shielding.
Figure 22C:
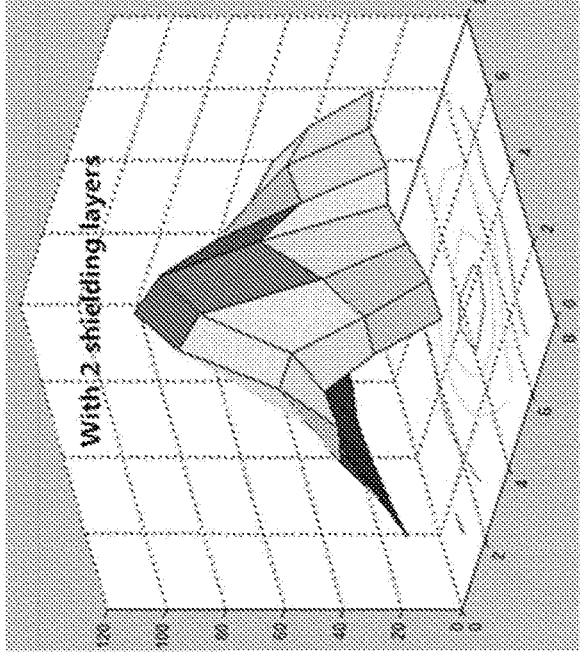
FIG. 22(c) shows field distribution with 2 layers of shielding.

With the same structure, an in accordance with further aspects of an embodiment of the invention, one or more passive shields may be used to achieve a focusing effect. FIG. 19 (a) shows induced current in a conductive wire. Although the applied magnetic field is pointing towards the same direction, with increasing or decreasing magnetic field the induced current in the wire can flow along different (opposite) directions. As shown in FIG. 19 (b), a highly conductive (non-magnetic) plate may be used to create a shield for a transient magnetic field. The induced current will produce a counter transient magnetic field, which will always be in the direction against the initiation transient magnetic field. A summation of the initial and induced magnetic fields will cancel out or distort some parts of the initial applied field.

FIGS. 20(a)-(c) shows how the magnetic shield configured as described above produces an induced counter field to distort the original field and eventually achieve a focusing effect. FIG. 20(a) shows an initial transient magnetic field. FIG. 20(b) shows the induced current generated by the transient magnetic field from an array of conductive rings or disks. FIG. 20(c) shows that the summation of the initial transient magnetic field and the induced transient magnetic field produce a combined field that is more focused in the center region.

To implement the principle/summation shown in FIGS. 20(a)-(c), the inventors herein have built an iron core stimulator with a structure as shown in FIG. 21(a) which has a pair of coils 2102 and a shield array 2104. It is important to note that the system may work even without an iron core, but such a system would require more current (although there will be no magnetic saturation effect with an air core instead of an iron core). FIG. 21(b) shows an example configuration for metal shield array 2104 which is composed of, by way of non-limiting example, 4 layers of metal rings or disks (although any number of layers, size, number and thickness of rings or disks may be provided within the spirit and scope of the invention). FIG. 21(c) shows the implemented one-coil-pair stimulator (shown generally at 2100), which has an iron core 2101 which, in this exemplary configuration, is formed of layers of iron sheets obtained from electrical transformers. The resulting magnetic field is confined in the iron core most of the time. The field spreads in the air between the two coils 2102 following an $r^2$ spreading rate, where r is the distance away from iron pole facets into air. Thus, the shields are used to achieve focusing of the magnetic field. FIGS. 21 (d)-(f) show examples of varying types of shields made of arrays 2104 of metal rings or disks.

As described above, arrays 2104 of small rings or disks are used, and none of them (i.e. rings or disks) is large enough to pass the middle center of the stimulator coil pair 2102 so that no induced current loop will enclose the center. Any ring or disk that would enclose the middle center would produce a counter field that will reduce magnetic field in the center, thereby defocusing the field.

Configurations of rings and disk, such as the ones described in this disclosure and the ones shown in FIG. 21, may be used in conjunction with any of the magnetic stimulators disclosed by this application (e.g. the stimulators in FIGS. 2, 4, 10, 14 and 21). For example, disk and ring configurations such as those shown in FIGS. 21(d)-(f) may be disposed in the magnetic stimulator shown in FIG. 14 at the positions shown by elements 145.

FIG. 22 shows measured induced electric field strength distribution along the x-y planes (perpendicular to the up-down, z-direction) in the middle plane between the two (top and bottom) coils of the coil configuration shown by FIGS. 21(a) and 21(c). FIG. 22(a) shows the measured field for an apparatus configuration that does not include any shield. FIG. 22(b) shows the field for a configuration including one layer of shielding. FIG. 22(c) shows the field for a configuration including 2 layers of shielding, and FIG. 22 (d) shows the field for a configuration including 4 layers of shielding. As can be seen clearly in FIGS. 22(a)-(d), the field is better focused with increasing the number of shield layers. The spot size shrinks down to ~7 mm when four layers of shielding are used. By manipulating the combinations of shields and coils, the spot size can be further reduced or increased based on specific clinical applications.

Figure 23:
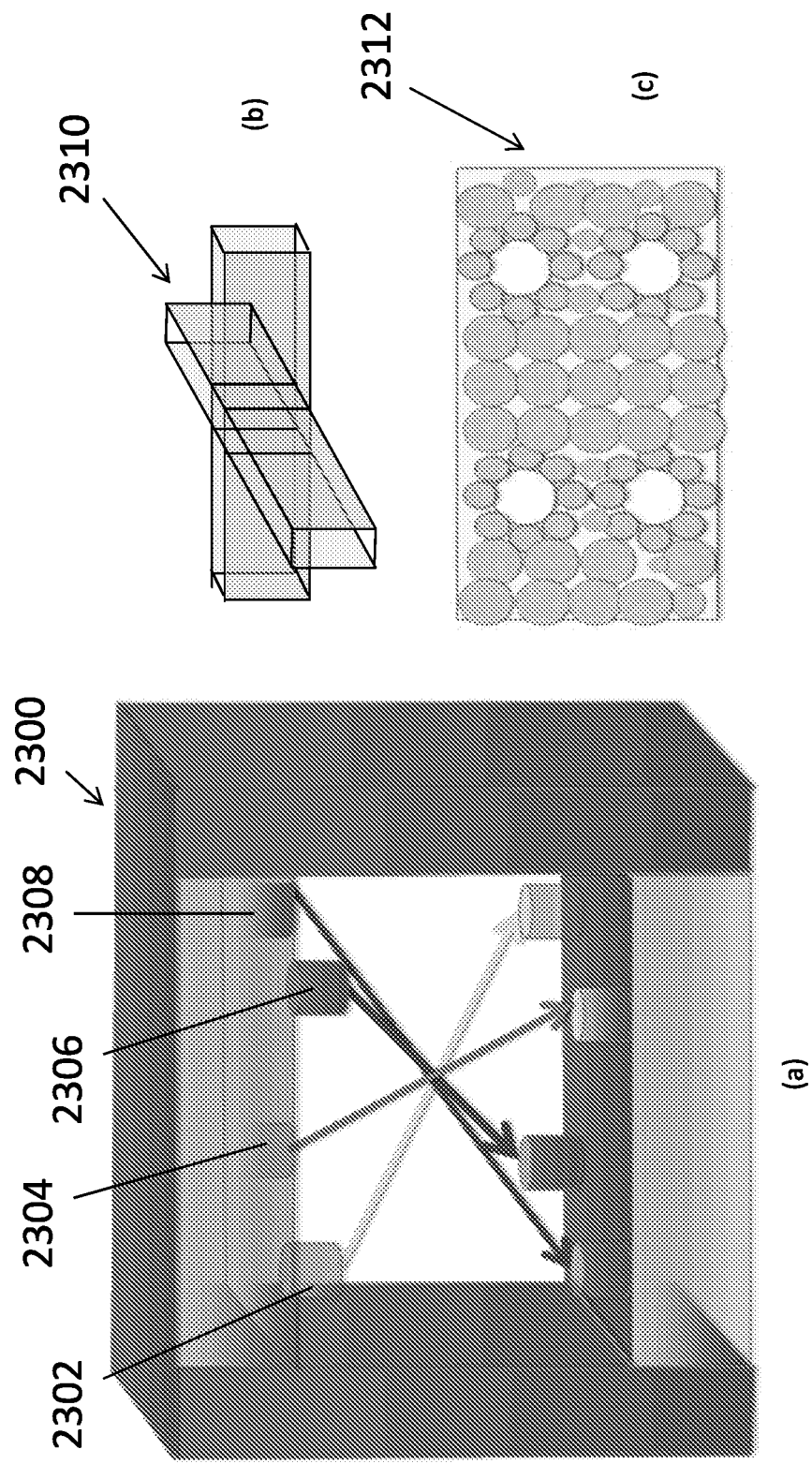
FIG. 23(a) is a schematic view of an exemplary stimulator with 4 coil pairs in accordance with certain aspects of an embodiment of the invention.
FIG. 23(b) is a schematic view of an exemplary shield for use with the stimulator of FIG. 23(a) to block transient magnetic field among the top coils or among the bottom coils.
FIG. 23(c) is a schematic view of an exemplary shield for use with the stimulator of FIG. 23(a) to help focus the magnetic field.

FIG. 23(a) shows an exemplary embodiment of a multi-pole stimulator (shown generally at 2300) including 4 coil pairs 2302, 2304, 2306 and 2308. An electrical current pulse can be sent to each diagonal pair in sequence such as to complete a cycle of 4 transient pulses (applied in the region between the four coil pairs—as shown by the arrows in FIG. 23(a)) within less than 1 ms. None of the transient pulses (schematically depicted as the arrows in FIG. 23(a)) can create sufficient magnetic field to reach action potential threshold (see FIG. 9 and the related discussion relating to action potential threshold). Rather, only the region at the cross point of the four arrows will reach the action potential threshold. FIG. 23(b) shows an exemplary shield 2310 which may be used to block transient magnetic between the top coils (or between the bottom coils) of multi-pole stimulator 2300. FIG. 23 (c) shows an exemplary layer of shielding 2312 that can be used under the 4-port stimulator structure, and that may help to focus the magnetic field. The skilled artisan would understand that the above embodiments are only exemplary, and that many more coil pairs and different combinations of size and shape of coil pairs can be configured without departing from the spirit and scope of the invention. Further, electrical current pulses can be sent in different intensities, durations, and intervals to achieve desired triangulation or summation spatially and temporally with minimal effects on areas outside of the triangulated region.

The above coil configurations and pulse sequences may be used in conjunction with any of the magnetic stimulators disclosed by this application (e.g. the stimulators in FIGS. 2, 4, 10, 14 and 21). For example, the coils of the magnetic stimulator shown in FIG. 14 may be fired diagonally such as to generate pulse sequences and pulse superposition as described above.

Multiple air-cooled coil pair arrays (as shown in FIGS. 17(a)-(f) and 18(a)-(b)) and multiple shield arrays (FIGS. 19(a)-(b) and 20(a)-(c)) are two exemplary implementations of using a summation of spatial Fourier components of magnetic field generators to build magnetic holes. Other implementation methods, such as superconducting coil arrays, super-magnet arrays, etc., may also be able to achieve the same goal of building magnetic holes or any other shapes of magnetic field distribution following the same spatial Fourier composite principle. Thus, the methods set forth herein cover wider implications for building any geometric shape of magnetic field distribution for electrical current confinement applications.

(J). Method and Apparatus Using Parallel Connection to Remove the Need of Extreme High Voltage in TMS Devices.

The method and apparatus disclosed hereinafter make possible the use of a scalable and relatively small voltage (driving the coil system) to achieve the magnetic fields and induced currents necessary for implementing the proposed TMS apparatus and method.

The magnetic field generated by a coil with an iron core is $B=n\mu i$, where n is the number of coil turns, the permeability $\mu=\mu_o\mu_r$ and $\mu_o$ is the permeability of air and $\mu_r$ is the relative permeability. For iron the $\mu_r$ can be 50,000 to 1 million depending on the purity of the iron core. The proposed stimulator structure has the advantage to produce $n \times \mu_r$ times stronger magnetic field with the same driving current, i. However, the structure will need a higher driving voltage due to the increasing inductance caused by increasing n and $\mu$, since $V=j\omega LI$ and the inductance, L, is $L=n^2 \mu A/l$ where A is the iron core cross section area and l is the length.

A traditional single coil magnetic field generator may include a single coil L 2102 wrapped around an iron core 2101 and connected to a voltage source V as shown by FIG. 24(a). To reduce the driving voltage, the single coil (as shown by L 2102 in FIG. 24(a)) is subdivided in multiple smaller coils (as shown by L1, L2, and L3, all labeled 2102(a) in FIG. 24(b)). The multiple smaller coils 2102(a) are connected to the voltage source V in parallel as shown in FIG. 24 (b). To obtain the same amount of total current circuiting the pole, the parallel connection structure requires much lower voltage. The parallel connection structure shown by FIG. 24(b) requires a significantly lower applied voltage than the single coil structure in FIG. 24(a) for obtaining the same amount of total current circuiting the pole. In other words, the same TMS effects may be obtained by using a lower applied voltage V with the multi coils structure in FIG. 24(b) as the TMS effect that would be obtained when using a higher applied voltage with the single coil structure in FIG. 24(a), as explained in the following.

$$B=N_0\mu i=\mu I (N_0 i=I)$$

To achieve the same peak B, the same amount of total current I needs to be supplied to the coil(s) surrounding the iron core.

$$m*n=N_0$$

$N_0$ is the total number of turns, which is subdivided to m coils each with n turns, and drive the m coils in parallel with one single voltage.

$$L_{eff}=(L_1+((m-1)M_1)/m$$

Here, M1 is the mutual inductance between any of two individual small coils, which is approximately equal to $M_1=\sqrt{L_1 L_1}=L_1$. Since for each coil there are (m−1) other coils to interact and to generate mutual inductance, we need to multiply (m−1) times. Thus, the final effective inductance is reflected by the following:

$$L_{eff}=mL_1/m=L_1$$

$$I=V/(\omega L_{eff})=(V)/(\omega L_1)$$

$$L_1=n^2\mu A/l$$

where I is the total (overall) current, V is the overall voltage, $\omega$ is signal frequency, $\mu$ is the permeability, A is the cross-sectional area of the inductor, and l is the length of the inductor.

$$I=(Vl)/(\omega n^2 \mu A)$$

Thus, with a fixed final total current I, we can obtain the voltage as $$V=I\omega n^2\mu A/l$$

I is assumed to be a constant if peak B is set. Thus, by reducing n (and increasing m), we can reduce V to a small number. n will be limited by how well the wire can uniformly cover the full length of the inductor l, since the inductance of the inductor is formulated by assuming it is fully and uniformed covered by the coil wire. If it is not the case the inductance will increase.

FIG. 25(a) shows 3 different wire wrappings and connection to the stimulator shown in FIG. 21(c), with the measured results of their generated B-field shown in FIGS. 25(b)-(d). In FIGS. 25(b)-(d), the yellow trace shows the driving voltage signal into the coils, whereas the blue traces show the generated magnetic/electric field signals for different coil structures and connections. FIG. 25(b) shows the results of using a 100 turn single coil. FIG. 25(c) shows the result of using 5 parallel coils each with 20 turns of wire. FIG. 25(d) shows the result of using a 10 parallel coils each with 10 turns of wire. As seen in these figures, the 100 turn coil has a larger resistance and the generated transient B-field is lower. By sub-dividing the 100 turn coil to 5 coils each with 20 turns, or subdividing to 10 coils each with 10 turns of wiring, the equivalent inductance and impedance drop and with the same voltage the transient increases. Thus, a higher magnetic field is generated.

In summary, the parallel connection method can solve the problem of a higher voltage requirement of the TMS structure described herein. It provides a flexibility to use any commercially available insulated-gate bipolar transistor (IGBT) to drive the coil system described herein.

The above methods for stimulating the brain may be used separately, simultaneously, or in various spatial and temporal combinations, such as to achieve the desired brain stimulation.

While the exemplary embodiments have been shown and described, it will be understood by those skilled in the art that various changes in form and details may be made thereto without departing from the spirit and scope of the present disclosure as defined by the appended claims.

In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. A system for controlling magnetic fields in a target volume inside of a patient's body, comprising:
   a first magnetic field source comprising at least a first pair of magnetic coils disposed on an external housing and positioned a distance apart from one another to define an open space between said first pair of magnetic coils, wherein said open space is sized to receive a portion of a patient's body, said first pair of magnetic coils being configured to generate a first magnetic field extending through said open space so as to intercept said portion of a patient's body;
   a second magnetic field source of a different size from said first magnetic field source and being configured to superpose with the first magnetic field and conform a shape of a resulting combined magnetic field to a predetermined desired shape at a target location at which said combined magnetic field interacts with said portion of a patient's body and at any depth into said portion of a patient's body that is positioned in said open space, said second magnetic field source further comprising a magnetic shield comprising an array of one or more conductive discs positioned between said first pair of magnetic coils, wherein said array of conductive discs further comprises a plurality of vertically stacked metal discs;
   a power source in electrical communication with said first magnetic field source; and
   a processor in electrical communication with said power source.

2. The system of claim 1, wherein said second magnetic field source is configured to produce a second magnetic field that in combination with said first magnetic field generates a magnetic hole at said target location.

3. The system of claim 2, wherein said second magnetic field source further comprises a second set of magnetic coils, wherein each of said second magnetic coils is positioned within a circumference of one of said first magnetic coils, and wherein said second set of magnetic coils is configured to generate a magnetic field that is opposite to said first magnetic field.

4. The system of claim 3, further comprising a third set of magnetic coils, wherein each of said third magnetic coils is positioned between one of said first magnetic coils and one of said second magnetic coils.

5. The system of claim 1, wherein said second magnetic field source is configured to produce a second magnetic field that in combination with said first magnetic field generates a concentrated magnetic field at said target location, wherein said concentrated magnetic field is of greater magnitude than all other regions of a combined magnetic field produced by said first and second magnetic field sources.

6. The system of claim 5, wherein said second magnetic field source further comprises a second set of magnetic coils, wherein each of said second magnetic coils is positioned within a circumference of one of said first magnetic coils, and wherein said second set of magnetic coils is configured to generate a magnetic field that is parallel to said first magnetic field.

7. The system of claim 6, further comprising a third set of magnetic coils, wherein each of said third magnetic coils is positioned between one of said first magnetic coils and one of said second magnetic coils.

8. The system of claim 1, wherein said array of conductive discs further comprises a plurality of horizontally aligned metal discs.

9. The system of claim 1, wherein said discs are positioned with respect to said first magnetic coils so that no portion of a disc extends into a midpoint of said first magnetic field.

10. The system of claim 1, said first magnetic field source comprising a plurality of pairs of first magnetic coils.

11. The system of claim 10, wherein said processor is configured to control said power source to sequentially direct electrical current to each pair of first magnetic coils in a cycle of transient pulses.

12. The system of claim 11, wherein none of said transient pulses is sufficient to cause a pair of said first magnetic coils to generate a magnetic field of sufficient magnitude to trigger neuronal firing within said target region.

13. The system of claim 12, wherein said processor is configured to control said power source to cause said cycle of transient pulses to generate a magnetic field of sufficient magnitude to trigger neuronal firing within said target region.

14. The system of claim 1, wherein said first pair of magnetic coils further comprises an iron core and a plurality of independent wire coils extending around at least a portion of said iron core.

15. The system of claim 14, wherein said plurality of independent wire coils are electrically connected to a voltage source in parallel.

* * * * *